US011179535B2

(12) United States Patent
McAuley et al.

(10) Patent No.: US 11,179,535 B2
(45) Date of Patent: *Nov. 23, 2021

(54) NASAL PILLOWS FOR A PATIENT INTERFACE

(71) Applicant: Fisher & Paykel Healthcare Limited, Auckland (NZ)

(72) Inventors: Alastair Edwin McAuley, Auckland (NZ); Craig Robert Prentice, Auckland (NZ); Rory Alexander Monro, London (GB); Isaac Tristram Tane Mason, Wales (GB); Nadjean Maurice Gabriel Geslain, Bordeaux (FR)

(73) Assignee: Fisher & Paykel Healthcare Limited, Auckland (NZ)

( * ) Notice: Subject to any disclaimer, the term of this patent is extended or adjusted under 35 U.S.C. 154(b) by 588 days.

This patent is subject to a terminal disclaimer.

(21) Appl. No.: 15/905,644

(22) Filed: Feb. 26, 2018

(65) Prior Publication Data

US 2019/0030273 A1 Jan. 31, 2019

Related U.S. Application Data

(63) Continuation of application No. 15/610,530, filed on May 31, 2017, now Pat. No. 9,907,925, which is a (Continued)

(51) Int. Cl.
*A61M 16/06* (2006.01)
*A61M 16/08* (2006.01)

(52) U.S. Cl.
CPC .... *A61M 16/0666* (2013.01); *A61M 16/0611* (2014.02); *A61M 16/0683* (2013.01);
(Continued)

(58) Field of Classification Search
CPC .......... A61M 16/0666; A61M 16/0672; A61M 16/0683; A61M 2016/0661; A61M 16/06;
(Continued)

(56) References Cited

U.S. PATENT DOCUMENTS 301,111 A 7/1884 Genese
472,238 A 4/1892 Van Orden
(Continued)

FOREIGN PATENT DOCUMENTS

AU 2003246441 12/2003
CA 1311662 12/1992
(Continued)

OTHER PUBLICATIONS

U.S. Appl. No. 60/493,515, filed Aug. 8, 2002, Sleeper et al.
(Continued)

*Primary Examiner* — Michael J Tsai
(74) *Attorney, Agent, or Firm* — Knobbe, Martens, Olson & Bear LLP

(57) ABSTRACT

A nasal pillow section for use as part of an apparatus for providing a stream of gases to a user, the pillow section in use located in front of the upper lip and below the nostrils of a user, the pillow section comprising a pillow gasket having a gases aperture which receives a stream of gases in use, and nasal pillows fluidically connected to the pillow gasket which are adapted to substantially seal against the nostrils of a user in use, so that substantially the whole of the stream of gases entering the gasket through the aperture passes into the nasal pillows from the pillow gasket and is delivered to the user, the lower inner surface of the pillow gasket shaped so that in use contact between the upper lip of a user and the pillow gasket is minimised.

13 Claims, 17 Drawing Sheets

Related U.S. Application Data continuation of application No. 13/123,503, filed as application No. PCT/NZ2009/000219 on Oct. 9, 2009, now Pat. No. 9,901,700.

(60) Provisional application No. 61/104,377, filed on Oct. 10, 2008.

(52) U.S. Cl.
CPC .... *A61M 16/0816* (2013.01); *A61M 16/0825* (2014.02); *A61M 16/0875* (2013.01)

(58) Field of Classification Search
CPC .......... A61M 16/0605; A61M 16/0616; A61M 2210/0618
See application file for complete search history.

(56) References Cited

U.S. PATENT DOCUMENTS

| | | |
|---|---|---|
| 577,926 A | 3/1897 | Miller |
| 718,470 A | 1/1903 | Jones |
| 751,091 A | 2/1904 | Moran |
| 770,013 A | 9/1904 | Linn |
| 1,635,545 A | 7/1927 | Drager |
| 2,126,755 A | 8/1938 | Dreyfus |
| 2,228,218 A | 1/1941 | Schwartz |
| 2,241,535 A | 5/1941 | Boothby et al. |
| 2,296,150 A | 9/1942 | Dockson et al. |
| 2,353,643 A | 7/1944 | Bulbulian |
| 2,359,506 A | 10/1944 | Battley et al. |
| 2,388,604 A | 11/1945 | Eisenbud |
| 2,452,845 A | 11/1948 | Fisher |
| 2,508,050 A | 5/1950 | Valente |
| 2,693,800 A | 11/1954 | Caldwell |
| 2,738,788 A | 3/1956 | Matheson et al. |
| 2,843,121 A | 7/1958 | Hudson |
| 2,859,748 A | 11/1958 | Hudson |
| 2,875,759 A | 3/1959 | Galleher |
| 2,894,506 A | 7/1959 | Rose |
| 2,939,458 A | 6/1960 | Lundquist |
| 3,424,633 A | 1/1969 | Corrigall et al. |
| 3,490,452 A | 1/1970 | Greenfield |
| 3,599,635 A | 8/1971 | Kenneth |
| 3,682,171 A | 8/1972 | Dali et all |
| 3,834,682 A | 9/1974 | McPhee |
| 3,850,171 A | 11/1974 | Ball et al. |
| 3,894,562 A | 7/1975 | Mosley et al. |
| 3,972,321 A | 8/1976 | Proctor |
| 3,977,432 A | 8/1976 | Vidal |
| 3,992,720 A | 11/1976 | Nicolinas |
| 4,090,510 A | 5/1978 | Segersten |
| D250,047 S | 10/1978 | Lewis et al. |
| D250,131 S | 10/1978 | Lewis et al. |
| 4,127,130 A | 11/1978 | Naysmith |
| 4,150,464 A | 4/1979 | Tracy |
| D252,322 S | 7/1979 | Johnson |
| 4,201,205 A | 5/1980 | Bartholomew |
| 4,258,710 A | 3/1981 | Reber |
| 4,266,540 A | 5/1981 | Panzik et al. |
| 4,278,082 A | 7/1981 | Blackmer |
| 4,354,488 A | 10/1982 | Bartos |
| 4,367,735 A | 1/1983 | Dali |
| 4,378,011 A | 3/1983 | Warncke et al. |
| 4,437,462 A | 3/1984 | Piljay |
| 4,454,880 A | 6/1984 | Muto et al. |
| 4,574,799 A | 3/1986 | Warncke et al. |
| 4,603,602 A | 8/1986 | Montesi |
| 4,621,632 A | 11/1986 | Bartels et al. |
| 4,644,974 A | 2/1987 | Zingg |
| 4,676,241 A | 6/1987 | Webb et al. |
| D293,613 S | 1/1988 | Wingler |
| 4,753,233 A | 6/1988 | Grimes |
| 4,782,832 A | 11/1988 | Trimble et al. |
| 4,836,200 A | 6/1989 | Clark et al. |
| 4,856,508 A | 8/1989 | Tayebi |
| 4,907,584 A | 3/1990 | McGinnis |
| 4,915,104 A | 4/1990 | Marcy |
| 4,915,105 A | 4/1990 | Lee |
| 4,919,128 A | 4/1990 | Kopala et al. |
| 4,938,209 A | 7/1990 | Fry |
| 4,941,467 A | 7/1990 | Takata |
| 4,944,310 A | 7/1990 | Sullivan |
| D310,431 S | 9/1990 | Bellm |
| 4,958,658 A | 9/1990 | Zajac |
| 4,971,051 A | 11/1990 | Toffolon |
| 4,986,269 A | 1/1991 | Hakkinen |
| 5,010,925 A | 4/1991 | Atkinson et al. |
| 5,016,625 A | 5/1991 | Hsu et al. |
| 5,031,261 A | 7/1991 | Fenner |
| 5,042,478 A | 8/1991 | Kopala et al. |
| D320,677 S | 10/1991 | Kumagai et al. |
| D321,419 S | 11/1991 | Wallace |
| 5,062,421 A | 11/1991 | Burns et al. |
| 5,065,756 A | 11/1991 | Rapoport |
| D322,318 S | 12/1991 | Sullivan et al. |
| 5,074,297 A | 12/1991 | Venegas |
| 5,094,236 A | 3/1992 | Tayebi |
| 5,113,857 A | 5/1992 | Dickerman et al. |
| 5,121,745 A | 6/1992 | Israel et al. |
| 5,148,802 A | 9/1992 | Sanders et al. |
| 5,164,652 A | 11/1992 | Johnson et al. |
| 5,231,979 A | 8/1993 | Rose |
| 5,243,971 A | 9/1993 | Sullivan et al. |
| 5,245,995 A | 9/1993 | Sullivan et al. |
| D340,317 S | 10/1993 | Cole |
| 5,259,377 A | 11/1993 | Schroeder |
| 5,267,556 A | 12/1993 | Feng |
| 5,269,296 A | 12/1993 | Landis et al. |
| 5,315,859 A | 5/1994 | Schommer |
| 5,349,949 A | 9/1994 | Schegerin |
| 5,366,805 A | 11/1994 | Fujiki et al. |
| D354,128 S | 1/1995 | Rinehart |
| D355,484 S | 2/1995 | Rinehart |
| 5,400,776 A | 3/1995 | Bartholomew |
| 5,429,683 A | 7/1995 | Le Mitouard |
| 5,438,979 A | 8/1995 | Johnson et al. |
| 5,441,046 A | 8/1995 | Starr et al. |
| 5,449,206 A | 9/1995 | Lockwood |
| 5,449,234 A | 9/1995 | Gipp et al. |
| 5,458,202 A | 10/1995 | Fellows et al. |
| 5,460,174 A | 10/1995 | Chang |
| 5,477,852 A | 12/1995 | Landis et al. |
| 5,513,634 A | 5/1996 | Jackson |
| 5,518,802 A | 5/1996 | Colvin et al. |
| 5,533,506 A | 7/1996 | Wood |
| 5,542,128 A | 8/1996 | Lomas |
| 5,551,419 A | 9/1996 | Froehlich et al. |
| 5,558,090 A | 9/1996 | James |
| 5,570,689 A | 11/1996 | Starr et al. |
| 5,588,423 A | 12/1996 | Smith |
| 5,595,174 A | 1/1997 | Gwaltney |
| 5,601,078 A | 2/1997 | Schaller et al. |
| D378,610 S | 3/1997 | Reischel et al. |
| 5,649,532 A | 7/1997 | Griffiths |
| 5,657,752 A | 8/1997 | Landis et al. |
| 5,662,101 A | 9/1997 | Ogden et al. |
| 5,664,566 A | 9/1997 | Mcdonald et al. |
| 5,687,715 A | 11/1997 | Landis |
| 5,690,097 A | 11/1997 | Howard et al. |
| 5,724,965 A | 3/1998 | Handke et al. |
| 5,752,510 A | 5/1998 | Goldstein |
| 5,755,578 A | 5/1998 | Contant et al. |
| 5,806,727 A | 9/1998 | Joseph |
| 5,807,295 A | 9/1998 | Hutcheon et al. |
| 5,746,201 A | 12/1998 | Kidd |
| 5,857,460 A | 1/1999 | Popitz |
| 5,884,624 A | 3/1999 | Barnett et al. |
| 5,904,278 A | 5/1999 | Barlow et al. |
| 5,918,598 A | 7/1999 | Belfer |
| 5,921,239 A | 7/1999 | McCall et al. |
| 5,924,420 A | 7/1999 | Reischel |
| 5,941,245 A | 8/1999 | Hannah et al. |
| 5,943,473 A | 8/1999 | Levine |

(56) References Cited

U.S. PATENT DOCUMENTS

| | | |
|---|---|---|
| 5,953,763 A | 9/1999 | Gouget |
| 5,966,745 A | 10/1999 | Schwartz et al. |
| 6,016,804 A | 1/2000 | Gleason et al. |
| 6,017,315 A | 1/2000 | Starr et al. |
| 6,019,101 A | 2/2000 | Cotner et al. |
| 6,021,528 A | 2/2000 | Jurga |
| 6,039,044 A | 3/2000 | Sullivan |
| 6,050,260 A | 4/2000 | Daniell et al. |
| 6,112,746 A | 9/2000 | Kwok et al. |
| 6,116,235 A | 9/2000 | Walters et al. |
| 6,119,693 A | 9/2000 | Kwok et al. |
| 6,119,694 A | 9/2000 | Correa et al. |
| 6,135,109 A | 10/2000 | Blasdell et al. |
| 6,135,432 A | 10/2000 | Hebblewhite et al. |
| 6,192,886 B1 | 2/2001 | Rudolph |
| D440,302 S | 4/2001 | Wolfe |
| 6,272,933 B1 | 8/2001 | Gradon et al. |
| 6,298,850 B1 | 10/2001 | Argraves |
| 6,302,105 B1 | 10/2001 | Wickham et al. |
| 6,341,606 B1 | 1/2002 | Bordewick et al. |
| 6,347,631 B1 | 2/2002 | Hansen et al. |
| D455,891 S | 4/2002 | Biedrzycki |
| 6,398,197 B1 | 6/2002 | Dickinson et al. |
| 6,412,487 B1 | 7/2002 | Gunaratnam et al. |
| 6,412,488 B1 | 7/2002 | Barnett |
| 6,418,928 B1 | 7/2002 | Bordewick et al. |
| 6,427,694 B1 | 8/2002 | Hecker et al. |
| 6,431,172 B1 | 8/2002 | Bordewick |
| 6,435,181 B1 | 8/2002 | Jones, Jr. et al. |
| 6,439,234 B1 | 8/2002 | Curti et al. |
| 6,457,473 B1 | 10/2002 | Brostrom et al. |
| 6,467,483 B1 | 10/2002 | Kopacko et al. |
| 6,470,886 B1 | 10/2002 | Jestrabek-Hart |
| 6,478,026 B1 | 11/2002 | Wood |
| 6,484,725 B1 | 11/2002 | Chi et al. |
| 6,488,664 B1 | 12/2002 | Solomon et al. |
| 6,491,034 B1 | 12/2002 | Gunaratnam et al. |
| 6,513,526 B2 | 2/2003 | Kwok et al. |
| 6,526,978 B2 | 3/2003 | Dominguez |
| 6,530,373 B1 | 3/2003 | Patron et al. |
| 6,561,188 B1 | 5/2003 | Ellis |
| 6,561,190 B1 | 5/2003 | Kwok |
| 6,561,191 B1 | 5/2003 | Kwok |
| 6,581,594 B1 | 6/2003 | Drew et al. |
| 6,581,601 B2 | 6/2003 | Ziaee |
| 6,581,602 B2 | 6/2003 | Kwok et al. |
| 6,584,977 B1 | 7/2003 | Serowski |
| 6,588,424 B2 | 7/2003 | Bardel |
| 6,615,832 B1 | 9/2003 | Chen |
| 6,629,531 B2 | 10/2003 | Gleason et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,658 B1 | 11/2003 | Hill et al. |
| 6,651,663 B2 | 11/2003 | Barnett et al. |
| 6,659,102 B1 | 12/2003 | Sico |
| 6,662,803 B2 | 12/2003 | Gradon et al. |
| 6,668,828 B1 | 12/2003 | Figley et al. |
| D485,905 S | 1/2004 | Moore |
| 6,679,257 B1 | 1/2004 | Robertson et al. |
| 6,679,265 B2 | 1/2004 | Strickland et al. |
| 6,691,707 B1 | 2/2004 | Gunaratnam et al. |
| 6,712,072 B1 | 3/2004 | Lang |
| 6,736,139 B1 | 5/2004 | Wix |
| 6,772,761 B1 | 8/2004 | Rucker, Jr. |
| 6,796,308 B2 | 9/2004 | Gunaratnam et al. |
| 6,817,362 B2 | 11/2004 | Gelinas et al. |
| 6,823,869 B2 | 11/2004 | Raje et al. |
| 6,851,425 B2 | 2/2005 | Jaffre et al. |
| 6,851,428 B2 | 2/2005 | Dennis |
| 6,883,177 B1 | 4/2005 | Ouellette et al. |
| 6,892,729 B2 | 5/2005 | Smith et al. |
| 6,895,965 B2 | 5/2005 | Scarberry et al. |
| 6,907,882 B2 | 6/2005 | Ging et al. |
| 6,918,390 B2 | 7/2005 | Lithgow et al. |
| 6,951,218 B2 | 10/2005 | Gradon et al. |
| 6,953,354 B2 | 10/2005 | Edirisuriya et al. |
| 6,997,187 B2 | 2/2006 | Wood et al. |
| 7,004,165 B1 | 2/2006 | Salcido |
| 7,007,696 B2 | 3/2006 | Palkon et al. |
| 7,021,311 B2 | 4/2006 | Gunaratnam et al. |
| D520,140 S | 5/2006 | Chaggares |
| 7,066,179 B2 | 6/2006 | Eaton et al. |
| 7,077,126 B2 | 7/2006 | Kummer et al. |
| D526,094 S | 8/2006 | Chen |
| 7,096,864 B1 | 8/2006 | Mayer et al. |
| D533,269 S | 12/2006 | McAuley et al. |
| 7,178,525 B2 | 2/2007 | Matula, Jr. et al. |
| 7,178,528 B2 | 2/2007 | Lau |
| 7,201,169 B2 | 4/2007 | Wilkie et al. |
| 7,207,333 B2 | 4/2007 | Tohara |
| 7,210,481 B1 | 5/2007 | Lovell et al. |
| 7,219,669 B1 | 5/2007 | Lovell et al. |
| 7,225,811 B2 | 6/2007 | Ruiz et al. |
| 7,255,106 B2 | 8/2007 | Gallem et al. |
| 7,261,104 B2 | 8/2007 | Keifer |
| 7,287,528 B2 | 10/2007 | Ho et al. |
| 7,290,546 B2 | 11/2007 | Sprinkle et al. |
| 7,296,575 B1 | 11/2007 | Radney |
| 7,318,437 B2 | 1/2008 | Gunaratnam et al. |
| 7,353,827 B2 | 4/2008 | Geist |
| 7,357,136 B2 | 4/2008 | Ho et al. |
| 7,406,966 B2 | 8/2008 | Wondka et al. |
| 7,448,386 B2 | 11/2008 | Ho et al. |
| 7,487,772 B2 | 2/2009 | Ging et al. |
| 7,493,902 B2 | 2/2009 | White et al. |
| D589,139 S | 3/2009 | Guney |
| 7,523,754 B2 | 4/2009 | Lithgow et al. |
| D595,841 S | 7/2009 | McAuley et al. |
| 7,562,658 B2 | 7/2009 | Madaus et al. |
| 7,597,100 B2 | 10/2009 | Ging |
| 7,640,934 B2 | 1/2010 | Zollinger et al. |
| 7,658,189 B2 | 2/2010 | Davidson et al. |
| 7,665,464 B2 | 2/2010 | Kopacko et al. |
| D612,933 S | 3/2010 | Prentice |
| 7,681,575 B2 | 3/2010 | Wixey et al. |
| 7,694,677 B2 | 4/2010 | Tang |
| 7,703,457 B2 | 4/2010 | Barnett et al. |
| 7,708,017 B2 * | 5/2010 | Davidson .......... A61M 16/0622 128/206.24 |
| 7,753,051 B2 | 7/2010 | Burrow et al. |
| D623,288 S | 9/2010 | Lubke |
| 7,814,911 B2 | 10/2010 | Bordewick et al. |
| 7,827,990 B1 | 11/2010 | Melidis et al. |
| 7,856,982 B2 | 12/2010 | Matula et al. |
| 7,877,817 B1 | 2/2011 | Ho |
| 7,896,003 B2 | 3/2011 | Matula et al. |
| 7,931,024 B2 | 4/2011 | Ho et al. |
| 7,934,501 B2 | 5/2011 | Fu |
| 7,942,150 B2 | 5/2011 | Guney et al. |
| 7,992,560 B2 | 8/2011 | Burton et al. |
| 8,042,539 B2 | 10/2011 | Chandran et al. |
| 8,042,541 B2 | 10/2011 | Amarasinghe et al. |
| 8,109,271 B2 | 2/2012 | Vandine et al. |
| 8,136,524 B2 | 3/2012 | Ging et al. |
| 8,136,525 B2 | 3/2012 | Lubke et al. |
| 8,171,933 B2 | 5/2012 | Xue et al. |
| D661,796 S | 6/2012 | Andrews et al. |
| 8,245,711 B2 | 8/2012 | Matula et al. |
| 8,371,302 B2 | 2/2013 | Ging et al. |
| 8,397,727 B2 | 3/2013 | Ng et al. |
| 8,443,807 B2 | 5/2013 | McAuley et al. |
| D686,313 S | 7/2013 | Matula et al. |
| 8,479,726 B2 | 7/2013 | McAuley |
| 8,479,741 B2 | 7/2013 | McAuley et al. |
| 8,567,404 B2 | 10/2013 | Davidson et al. |
| 8,631,793 B2 | 1/2014 | Omura et al. |
| 8,631,799 B2 | 1/2014 | Davenport |
| 8,636,005 B2 | 1/2014 | Gradon et al. |
| 8,701,667 B1 | 4/2014 | Ho et al. |
| 8,714,157 B2 | 5/2014 | McAuley et al. |
| 8,720,444 B2 | 5/2014 | Chang |
| 8,757,157 B2 | 6/2014 | Price et al. |

(56) References Cited

U.S. PATENT DOCUMENTS

| | | | |
|---|---|---|---|
| 8,783,257 B2* | 7/2014 | McAuley | A61M 16/024 128/207.18 |
| 8,869,797 B2 | 10/2014 | Davidson et al. | |
| 8,869,798 B2 | 10/2014 | Wells et al. | |
| 8,875,709 B2 | 11/2014 | Davidson et al. | |
| 8,944,061 B2 | 2/2015 | D'Souza et al. | |
| 8,950,404 B2 | 2/2015 | Formica et al. | |
| 8,960,196 B2 | 2/2015 | Henry | |
| 9,010,331 B2 | 4/2015 | Lang et al. | |
| 9,027,556 B2 | 5/2015 | Ng et al. | |
| 9,032,955 B2 | 5/2015 | Lubke et al. | |
| 9,032,956 B2 | 5/2015 | Scheiner et al. | |
| 9,072,852 B2 | 7/2015 | McAuley et al. | |
| 9,095,673 B2 | 8/2015 | Barlow et al. | |
| 9,119,929 B2 | 9/2015 | McAuley et al. | |
| 9,119,931 B2 | 9/2015 | D'Souza et al. | |
| 9,138,555 B2 | 9/2015 | McAuley et al. | |
| 9,149,596 B2 | 10/2015 | Valcic et al. | |
| 9,186,474 B1 | 11/2015 | Rollins | |
| 9,242,062 B2 | 1/2016 | Melidis et al. | |
| 9,292,799 B2 | 3/2016 | McAuley et al. | |
| 9,295,799 B2 | 3/2016 | McAuley et al. | |
| 9,302,065 B2 | 4/2016 | Smith et al. | |
| 9,320,566 B1 | 4/2016 | Alston, Jr. | |
| 9,320,866 B2 | 4/2016 | McAuley et al. | |
| 9,333,315 B2 | 5/2016 | McAuley et al. | |
| 9,339,622 B2 | 5/2016 | McAuley et al. | |
| 9,339,624 B2 | 5/2016 | McAuley | |
| 9,375,545 B2 | 6/2016 | Darkin et al. | |
| 9,381,316 B2 | 7/2016 | Ng et al. | |
| 9,457,162 B2 | 10/2016 | Ging et al. | |
| 9,486,601 B2 | 11/2016 | Stallard et al. | |
| 9,517,317 B2 | 12/2016 | McAuley et al. | |
| 9,522,246 B2 | 12/2016 | Frater et al. | |
| 9,539,405 B2 | 1/2017 | McAuley et al. | |
| 9,550,038 B2 | 1/2017 | McAuley et al. | |
| 9,561,338 B2 | 2/2017 | McAuley et al. | |
| 9,561,339 B2 | 2/2017 | McAuley et al. | |
| 9,744,385 B2 | 8/2017 | Henry et al. | |
| 9,884,160 B2 | 2/2018 | McAuley et al. | |
| 9,901,699 B2 | 2/2018 | Veliss et al. | |
| 9,901,700 B2 | 2/2018 | McAuley et al. | |
| 9,907,925 B2 | 3/2018 | McAuley et al. | |
| 9,974,914 B2 | 5/2018 | McAuley | |
| 10,080,856 B2 | 9/2018 | McLaren et al. | |
| 10,137,271 B2 | 11/2018 | McAuley et al. | |
| 10,201,678 B2 | 2/2019 | Guney et al. | |
| 10,252,015 B2 | 4/2019 | McAuley et al. | |
| 10,258,757 B2 | 4/2019 | Allan et al. | |
| 10,272,218 B2 | 4/2019 | McAuley et al. | |
| 10,328,226 B2 | 6/2019 | Allan et al. | |
| 10,363,387 B2 | 7/2019 | Allan et al. | |
| 10,384,029 B2 | 8/2019 | McAuley et al. | |
| 10,413,694 B2 | 9/2019 | Allan et al. | |
| 10,463,825 B2 | 11/2019 | McAuley et al. | |
| 10,742,451 B2 | 10/2020 | Allan et al. | |
| 10,821,251 B2 | 11/2020 | McAuley et al. | |
| 10,835,702 B2 | 11/2020 | McAuley et al. | |
| 10,842,964 B2 | 11/2020 | McAuley et al. | |
| 2001/0017134 A1 | 8/2001 | Bahr | |
| 2001/0020474 A1 | 9/2001 | Hecker et al. | |
| 2001/0029952 A1 | 10/2001 | Curran | |
| 2002/0014241 A1 | 2/2002 | Gradon et al. | |
| 2002/0020416 A1 | 2/2002 | Namey | |
| 2002/0026934 A1 | 3/2002 | Lithgow et al. | |
| 2002/0029780 A1 | 3/2002 | Frater et al. | |
| 2002/0039867 A1 | 4/2002 | Curro et al. | |
| 2002/0046755 A1 | 4/2002 | Voss | |
| 2002/0053347 A1 | 5/2002 | Ziaee | |
| 2002/0059935 A1 | 5/2002 | Wood | |
| 2002/0069467 A1 | 6/2002 | Immediato et al. | |
| 2002/0096176 A1 | 7/2002 | Gunaratnam et al. | |
| 2002/0096178 A1 | 7/2002 | Ziaee | |
| 2002/0100474 A1 | 8/2002 | Kellner et al. | |
| 2002/0100479 A1 | 8/2002 | Scarberry et al. | |
| 2002/0108613 A1 | 8/2002 | Gunaratnam et al. | |
| 2003/0005509 A1 | 1/2003 | Kelzer | |
| 2003/0005931 A1 | 1/2003 | Jaffre et al. | |
| 2003/0005933 A1 | 1/2003 | Izuchukwu | |
| 2003/0019495 A1 | 1/2003 | Palkon et al. | |
| 2003/0019496 A1 | 1/2003 | Kopacko et al. | |
| 2003/0029454 A1 | 2/2003 | Gelinas et al. | |
| 2003/0047185 A1 | 3/2003 | Olsen et al. | |
| 2003/0075180 A1 | 4/2003 | Raje | |
| 2003/0075182 A1 | 4/2003 | Heidmann et al. | |
| 2003/0079749 A1 | 5/2003 | Strickland et al. | |
| 2003/0084996 A1 | 5/2003 | Alberg et al. | |
| 2003/0089373 A1 | 5/2003 | Gradon et al. | |
| 2003/0094177 A1 | 5/2003 | Smith et al. | |
| 2003/0121519 A1 | 7/2003 | Estes et al. | |
| 2003/0149384 A1 | 8/2003 | Davis et al. | |
| 2003/0164170 A1 | 9/2003 | Drew et al. | |
| 2003/0172936 A1 | 9/2003 | Wilkie et al. | |
| 2003/0196655 A1 | 10/2003 | Ging et al. | |
| 2003/0196656 A1 | 10/2003 | Moore | |
| 2003/0196658 A1 | 10/2003 | Ging et al. | |
| 2003/0196659 A1 | 10/2003 | Gradon et al. | |
| 2003/0196664 A1 | 10/2003 | Jacobson | |
| 2003/0200970 A1 | 10/2003 | Stenzler et al. | |
| 2003/0217746 A1 | 11/2003 | Gradon et al. | |
| 2003/0221691 A1 | 12/2003 | Biener | |
| 2004/0011087 A1 | 1/2004 | Rebouillat et al. | |
| 2004/0025882 A1 | 2/2004 | Madaus et al. | |
| 2004/0035427 A1 | 2/2004 | Bordewick et al. | |
| 2004/0065328 A1 | 4/2004 | Amarasinghe et al. | |
| 2004/0067333 A1 | 4/2004 | Amarasinghe | |
| 2004/0092999 A1 | 5/2004 | Lojewski | |
| 2004/0094157 A1 | 5/2004 | Dantanarayana et al. | |
| 2004/0107968 A1 | 6/2004 | Griffiths | |
| 2004/0112377 A1 | 6/2004 | Amarasinghe et al. | |
| 2004/0112384 A1 | 6/2004 | Lithgow et al. | |
| 2004/0112385 A1 | 6/2004 | Drew | |
| 2004/0118406 A1 | 6/2004 | Lithgow | |
| 2004/0118412 A1 | 6/2004 | Piletti-Reyes | |
| 2004/0139973 A1 | 7/2004 | Wright | |
| 2004/0149280 A1 | 8/2004 | Semeniuk | |
| 2004/0182398 A1 | 9/2004 | Sprinkle et al. | |
| 2004/0211427 A1 | 10/2004 | Jones et al. | |
| 2004/0221850 A1 | 11/2004 | Ging et al. | |
| 2004/0226566 A1* | 11/2004 | Gunaratnam | A61M 16/0666 128/207.18 |
| 2004/0255949 A1 | 12/2004 | Lang et al. | |
| 2005/0011521 A1 | 1/2005 | Sprinkle et al. | |
| 2005/0011524 A1* | 1/2005 | Thomlinson | A61M 16/0666 128/207.18 |
| 2005/0016532 A1 | 1/2005 | Farrell | |
| 2005/0028822 A1* | 2/2005 | Sleeper | A61M 16/045 128/207.18 |
| 2005/0033247 A1 | 2/2005 | Thompson | |
| 2005/0045182 A1 | 3/2005 | Wood et al. | |
| 2005/0051177 A1 | 3/2005 | Wood | |
| 2005/0066976 A1 | 3/2005 | Wondka | |
| 2005/0076913 A1 | 4/2005 | Ho et al. | |
| 2005/0092327 A1 | 5/2005 | Fini et al. | |
| 2005/0098183 A1 | 5/2005 | Nash et al. | |
| 2005/0121037 A1 | 6/2005 | Wood | |
| 2005/0133038 A1 | 6/2005 | Rutter | |
| 2005/0150497 A1 | 7/2005 | Eifler et al. | |
| 2005/0155604 A1 | 7/2005 | Ging et al. | |
| 2005/0172969 A1 | 8/2005 | Ging | |
| 2005/0199239 A1 | 9/2005 | Lang et al. | |
| 2005/0199242 A1 | 9/2005 | Matula et al. | |
| 2005/0205096 A1 | 9/2005 | Matula | |
| 2005/0235999 A1 | 10/2005 | Wood et al. | |
| 2005/0241644 A1 | 11/2005 | Guney et al. | |
| 2006/0032504 A1 | 2/2006 | Burton et al. | |
| 2006/0042629 A1 | 3/2006 | Geist | |
| 2006/0042632 A1 | 3/2006 | Bishop et al. | |
| 2006/0054169 A1 | 3/2006 | Han et al. | |
| 2006/0060200 A1 | 3/2006 | Ho et al. | |
| 2006/0076019 A1 | 4/2006 | Ho | |
| 2006/0081250 A1 | 4/2006 | Bordewick et al. | |
| 2006/0081256 A1 | 4/2006 | Palmer | |
| 2006/0096598 A1 | 5/2006 | Ho et al. | |

(56) References Cited

U.S. PATENT DOCUMENTS

| | | |
|---|---|---|
| 2006/0107958 A1 | 5/2006 | Sleeper |
| 2006/0118117 A1 | 6/2006 | Berthon-Jones et al. |
| 2006/0124131 A1 | 6/2006 | Chandran |
| 2006/0130844 A1 | 6/2006 | Ho et al. |
| 2006/0137690 A1 | 6/2006 | Gunaratnam et al. |
| 2006/0169286 A1 | 8/2006 | Eifler et al. |
| 2006/0174887 A1 | 8/2006 | Chandran et al. |
| 2006/0196511 A1 | 9/2006 | Lau et al. |
| 2006/0201514 A1 | 9/2006 | Jones et al. |
| 2006/0207599 A1 | 9/2006 | Busch |
| 2006/0225740 A1 | 10/2006 | Eaton et al. |
| 2006/0231103 A1 | 10/2006 | Matula et al. |
| 2006/0237017 A1 | 10/2006 | Davidson et al. |
| 2006/0237018 A1 | 10/2006 | McAuley et al. |
| 2006/0249159 A1 | 11/2006 | Ho |
| 2006/0254593 A1 | 11/2006 | Chang |
| 2006/0266361 A1 | 11/2006 | Hernandez |
| 2006/0283458 A1 | 12/2006 | Woodard |
| 2006/0283459 A1 | 12/2006 | Geiselhart et al. |
| 2006/0283461 A1 | 12/2006 | Lubke et al. |
| 2007/0000492 A1 | 1/2007 | Hansel et al. |
| 2007/0010786 A1 | 1/2007 | Casey et al. |
| 2007/0044804 A1 | 3/2007 | Matula et al. |
| 2007/0062536 A1 | 3/2007 | McAuley |
| 2007/0089749 A1 | 4/2007 | Ho et al. |
| 2007/0107733 A1 | 5/2007 | Ho |
| 2007/0125384 A1 | 6/2007 | Zollinger et al. |
| 2007/0125385 A1 | 6/2007 | Ho et al. |
| 2007/0125387 A1 | 6/2007 | Zollinger et al. |
| 2007/0137653 A1 | 6/2007 | Wood |
| 2007/0142785 A1 | 6/2007 | Lundgaard et al. |
| 2007/0157353 A1 | 7/2007 | Guney et al. |
| 2007/0163600 A1 | 7/2007 | Hoffman |
| 2007/0174952 A1 | 8/2007 | Jacob |
| 2007/0175480 A1 | 8/2007 | Gradon et al. |
| 2007/0209663 A1 | 9/2007 | Marque et al. |
| 2007/0215161 A1 | 9/2007 | Frater et al. |
| 2007/0221227 A1 | 9/2007 | Ho |
| 2007/0227541 A1 | 10/2007 | Van Den |
| 2007/0272249 A1* | 11/2007 | Chandran ......... A61M 16/0666 128/206.28 |
| 2007/0295335 A1 | 12/2007 | Nashed |
| 2008/0035152 A1 | 2/2008 | Ho et al. |
| 2008/0041388 A1 | 2/2008 | McAuley et al. |
| 2008/0041393 A1 | 2/2008 | Bracken |
| 2008/0047560 A1 | 2/2008 | Veliss et al. |
| 2008/0060648 A1 | 3/2008 | Thornton et al. |
| 2008/0060653 A1 | 3/2008 | Hallett et al. |
| 2008/0060657 A1 | 3/2008 | McAuley et al. |
| 2008/0083412 A1 | 4/2008 | Henry et al. |
| 2008/0092905 A1* | 4/2008 | Gunaratnam ..... A61M 16/0666 128/207.18 |
| 2008/0099024 A1 | 5/2008 | Gunaratnam et al. |
| 2008/0105257 A1 | 5/2008 | Klasek et al. |
| 2008/0110464 A1 | 5/2008 | Davidson et al. |
| 2008/0135050 A1 | 6/2008 | Hitchcock |
| 2008/0142019 A1 | 6/2008 | Lewis |
| 2008/0171737 A1 | 7/2008 | Fensome |
| 2008/0178875 A1 | 7/2008 | Henry |
| 2008/0178886 A1 | 7/2008 | Lieberman et al. |
| 2008/0190432 A1 | 8/2008 | Blochlinger et al. |
| 2008/0190436 A1 | 8/2008 | Jaffe et al. |
| 2008/0196728 A1 | 8/2008 | Ho |
| 2008/0210241 A1 | 9/2008 | Schulz et al. |
| 2008/0223370 A1 | 9/2008 | Kim |
| 2008/0236586 A1 | 10/2008 | Mcdonald et al. |
| 2008/0257354 A1 | 10/2008 | Davidson |
| 2008/0264422 A1 | 10/2008 | Fishman |
| 2008/0271739 A1 | 11/2008 | Facer et al. |
| 2008/0276937 A1 | 11/2008 | Davidson et al. |
| 2008/0302366 A1 | 12/2008 | McGinnis et al. |
| 2008/0314388 A1 | 12/2008 | Brambilla et al. |
| 2008/0319334 A1 | 12/2008 | Yamamori |
| 2009/0014007 A1 | 1/2009 | Brambilla et al. |
| 2009/0032024 A1 | 2/2009 | Burz et al. |
| 2009/0044808 A1 | 2/2009 | Guney et al. |
| 2009/0078267 A1 | 3/2009 | Burz et al. |
| 2009/0107504 A1 | 4/2009 | McAuley et al. |
| 2009/0114227 A1 | 5/2009 | Gunaratnam et al. |
| 2009/0120442 A1 | 5/2009 | Ho |
| 2009/0126739 A1 | 5/2009 | Ng et al. |
| 2009/0133697 A1 | 5/2009 | Kwok et al. |
| 2009/0139527 A1 | 6/2009 | Ng et al. |
| 2009/0145429 A1 | 6/2009 | Ging et al. |
| 2009/0151729 A1 | 6/2009 | Judson et al. |
| 2009/0173349 A1 | 7/2009 | Hernandez et al. |
| 2009/0183734 A1 | 7/2009 | Kwok et al. |
| 2009/0183739 A1 | 7/2009 | Wondka |
| 2009/0211583 A1 | 8/2009 | Carroll |
| 2009/0223519 A1 | 9/2009 | Eifler et al. |
| 2010/0000538 A1 | 1/2010 | Edwards et al. |
| 2010/0000539 A1 | 1/2010 | Woodard |
| 2010/0000543 A1 | 1/2010 | Berthon-Jones et al. |
| 2010/0051031 A1 | 3/2010 | Lustenberger et al. |
| 2010/0051034 A1 | 3/2010 | Howard |
| 2010/0083969 A1 | 4/2010 | Crumblin |
| 2010/0108072 A1 | 5/2010 | D'Souza |
| 2010/0132717 A1 | 6/2010 | Davidson et al. |
| 2010/0154798 A1 | 6/2010 | Henry et al. |
| 2010/0170516 A1 | 7/2010 | Grane |
| 2010/0199992 A1 | 8/2010 | Ho |
| 2010/0229868 A1 | 9/2010 | Rummery et al. |
| 2010/0229872 A1 | 9/2010 | Ho |
| 2010/0258132 A1 | 10/2010 | Moore |
| 2010/0258136 A1 | 10/2010 | Doherty et al. |
| 2010/0294281 A1 | 11/2010 | Ho |
| 2010/0307502 A1 | 12/2010 | Rummery et al. |
| 2010/0313891 A1 | 12/2010 | Veliss et al. |
| 2010/0319700 A1 | 12/2010 | Ng et al. |
| 2010/0326445 A1 | 12/2010 | Veliss et al. |
| 2011/0067704 A1 | 3/2011 | Kooij |
| 2011/0072553 A1 | 3/2011 | Ho |
| 2011/0088699 A1 | 4/2011 | Skipper |
| 2011/0126838 A1 | 6/2011 | Alberici |
| 2011/0232649 A1 | 9/2011 | Collazo et al. |
| 2011/0259337 A1 | 10/2011 | Hitchcock |
| 2011/0265796 A1 | 11/2011 | Amarasinghe et al. |
| 2011/0290253 A1 | 12/2011 | McAuley |
| 2012/0125339 A1 | 5/2012 | Ho et al. |
| 2012/0132208 A1 | 5/2012 | Judson et al. |
| 2012/0132209 A1 | 5/2012 | Rummery |
| 2012/0138061 A1 | 6/2012 | Dravitzki et al. |
| 2012/0204879 A1 | 8/2012 | Cariola et al. |
| 2012/0285457 A1 | 11/2012 | Mansour et al. |
| 2012/0304999 A1 | 12/2012 | Swift et al. |
| 2012/0318265 A1 | 12/2012 | Amirav et al. |
| 2013/0133659 A1 | 5/2013 | Ng et al. |
| 2013/0133664 A1 | 5/2013 | Startare |
| 2013/0152918 A1 | 6/2013 | Rummery et al. |
| 2013/0160769 A1 | 6/2013 | Ng et al. |
| 2014/0026888 A1 | 1/2014 | Matula |
| 2014/0083428 A1 | 3/2014 | Rothermel et al. |
| 2014/0083430 A1 | 3/2014 | Matula, Jr. et al. |
| 2014/0137870 A1 | 5/2014 | Barlow et al. |
| 2014/0261432 A1 | 9/2014 | Eves et al. |
| 2014/0311492 A1 | 10/2014 | Stuebiger et al. |
| 2014/0338672 A1 | 11/2014 | D'Souza et al. |
| 2015/0033457 A1 | 2/2015 | Tryner et al. |
| 2015/0090266 A1 | 4/2015 | Melidis et al. |
| 2015/0246198 A1 | 9/2015 | Bearne et al. |
| 2015/0335846 A1 | 11/2015 | Romagnoli et al. |
| 2015/0352308 A1 | 12/2015 | Cullen et al. |
| 2015/0374944 A1 | 12/2015 | Edwards et al. |
| 2016/0001028 A1 | 1/2016 | McAuley et al. |
| 2016/0008558 A1 | 1/2016 | Huddart et al. |
| 2016/0015922 A1 | 1/2016 | Chodkowski et al. |
| 2016/0038707 A1 | 2/2016 | Allan et al. |
| 2016/0051786 A1 | 2/2016 | McAuley et al. |
| 2016/0213873 A1 | 7/2016 | McAuley et al. |
| 2016/0213874 A1 | 7/2016 | Davidson et al. |
| 2016/0296720 A1* | 10/2016 | Henry ............... A61M 16/0683 |
| 2017/0246411 A1 | 8/2017 | Mashal et al. |
| 2017/0304574 A1 | 10/2017 | McAuley et al. |
| 2017/0368288 A1 | 12/2017 | Stephens et al. |

(56) References Cited

U.S. PATENT DOCUMENTS

| | | |
|---|---|---|
| 2018/0250483 A1 | 9/2018 | Olsen et al. |
| 2018/0256844 A1 | 9/2018 | Galgali et al. |
| 2019/0001095 A1 | 1/2019 | Rose et al. |
| 2019/0030273 A1 | 1/2019 | McAuley et al. |
| 2019/0232010 A1 | 8/2019 | McAuley et al. |
| 2020/0016357 A1 | 1/2020 | McAuley et al. |
| 2020/0046928 A1 | 3/2020 | Allan |
| 2020/0108219 A1 | 4/2020 | McAuley et al. |
| 2020/0171260 A1 | 6/2020 | McLaren |
| 2020/0197644 A1 | 6/2020 | McAuley et al. |
| 2020/0268997 A1 | 8/2020 | McAuley et al. |
| 2020/0268998 A1 | 8/2020 | McAuley et al. |

FOREIGN PATENT DOCUMENTS

| | | |
|---|---|---|
| CA | 2648690 | 11/2007 |
| CD | 000966064-0001 | 9/2008 |
| CD | 000966064-0002 | 9/2008 |
| CD | 000966064-0003 | 9/2008 |
| CD | 000966064-0004 | 9/2008 |
| CD | 000966064-0017 | 9/2008 |
| CN | 2172538 | 7/1994 |
| CN | 1780265 | 12/2005 |
| CN | 1751149 | 3/2006 |
| CN | 1784250 | 6/2006 |
| CN | 1901961 | 1/2007 |
| CN | 1905917 | 1/2007 |
| CN | 101115521 | 1/2008 |
| CN | 100502972 | 6/2009 |
| CN | 101516300 | 8/2009 |
| CN | 101541380 | 9/2009 |
| CN | 101991897 | 3/2011 |
| DE | 895692 | 11/1953 |
| DE | 29723101 U1 | 7/1998 |
| DE | 19603949 | 11/1998 |
| DE | 10312881 | 5/2004 |
| DE | 102006011151 | 9/2007 |
| DE | 10 2009 016150 | 10/2010 |
| EP | 0 350 322 | 1/1990 |
| EP | 0 427 474 | 5/1991 |
| EP | 0 462 701 | 12/1991 |
| EP | 0 747 078 | 12/1996 |
| EP | 1 099 452 | 5/2001 |
| EP | 0 830 180 | 3/2002 |
| EP | 1 258 266 | 11/2002 |
| EP | 1 488 820 | 12/2004 |
| EP | 1 582 231 | 10/2005 |
| EP | 2 042 209 | 4/2009 |
| EP | 2 130 563 | 12/2009 |
| EP | 2 145 645 | 1/2010 |
| EP | 1 753 495 | 9/2010 |
| EP | 1 481 702 | 9/2012 |
| EP | 2 749 176 | 7/2014 |
| EP | 1 646 910 | 8/2015 |
| EP | 2 022 528 | 3/2016 |
| EP | 2 451 518 | 10/2017 |
| FR | 2658725 | 8/1991 |
| FR | 2749176 | 12/1997 |
| GB | 190224431 | 12/1902 |
| GB | 880824 | 10/1961 |
| GB | 979357 | 1/1965 |
| GB | 1467828 | 3/1977 |
| GB | 2133275 | 7/1984 |
| GB | 2173274 | 10/1986 |
| GB | 2186801 | 8/1987 |
| JP | 62-024721 | 2/1987 |
| JP | H09-010311 | 1/1997 |
| JP | 2000-325481 | 11/2000 |
| JP | 2004-016488 | 1/2004 |
| JP | 2005-529687 | 10/2005 |
| JP | 2005-537906 | 12/2005 |
| JP | 2007-516750 | 6/2007 |
| NZ | 531332 | 2/2004 |
| NZ | 534606 | 8/2004 |
| NZ | 528029 | 3/2005 |
| NZ | 548575 | 7/2006 |
| NZ | 551103 | 11/2006 |
| WO | WO 82/003548 | 10/1982 |
| WO | WO 97/32494 | 9/1997 |
| WO | WO 98/04310 | 2/1998 |
| WO | WO 98/04311 | 2/1998 |
| WO | WO 98/018514 | 5/1998 |
| WO | WO 98/024499 | 6/1998 |
| WO | WO 98/048878 | 11/1998 |
| WO | WO 98/57691 | 12/1998 |
| WO | WO 99/04842 | 2/1999 |
| WO | WO 99/43375 | 9/1999 |
| WO | WO 99/058181 | 11/1999 |
| WO | WO 99/058198 | 11/1999 |
| WO | WO 00/050122 | 8/2000 |
| WO | WO 00/057942 | 10/2000 |
| WO | WO 00/069497 | 11/2000 |
| WO | WO 00/74509 | 12/2000 |
| WO | WO 00/074758 | 12/2000 |
| WO | WO 00/078384 | 12/2000 |
| WO | WO 01/00266 | 1/2001 |
| WO | WO 01/32250 | 5/2001 |
| WO | WO 01/041854 | 6/2001 |
| WO | WO 01/058293 | 8/2001 |
| WO | WO 01/062326 | 8/2001 |
| WO | WO 01/94721 | 12/2001 |
| WO | WO 01/097892 | 12/2001 |
| WO | WO 01/97892 | 12/2001 |
| WO | WO 01/097893 | 12/2001 |
| WO | WO 02/005883 | 1/2002 |
| WO | WO 02/011804 | 2/2002 |
| WO | WO 02/047749 | 6/2002 |
| WO | WO 02/074372 | 9/2002 |
| WO | WO 03/035156 | 5/2003 |
| WO | WO 03/092755 | 11/2003 |
| WO | WO 04/007010 | 1/2004 |
| WO | WO 04/096332 | 1/2004 |
| WO | WO 04/012803 | 2/2004 |
| WO | WO 04/022147 | 3/2004 |
| WO | WO 04/030736 | 4/2004 |
| WO | WO 04/041341 | 5/2004 |
| WO | WO 04/041342 | 5/2004 |
| WO | WO 04/071565 | 8/2004 |
| WO | WO 04/073777 | 9/2004 |
| WO | WO 04/073778 | 9/2004 |
| WO | WO 05/010608 | 2/2005 |
| WO | WO 05/016403 | 2/2005 |
| WO | WO 05/018523 | 3/2005 |
| WO | WO 05/021075 | 3/2005 |
| WO | WO 05/051468 | 6/2005 |
| WO | WO 05/063326 | 7/2005 |
| WO | WO 05/063328 | 7/2005 |
| WO | WO 05/079726 | 9/2005 |
| WO | WO 05/086943 | 9/2005 |
| WO | WO 05/086946 | 9/2005 |
| WO | WO 05/097247 | 10/2005 |
| WO | WO 05/123166 | 12/2005 |
| WO | WO 06/000046 | 1/2006 |
| WO | WO 06/050559 | 5/2006 |
| WO | WO 06/069415 | 7/2006 |
| WO | WO 06/074513 | 7/2006 |
| WO | WO 06/074514 | 7/2006 |
| WO | WO 06/074515 | 7/2006 |
| WO | WO 06/096924 | 9/2006 |
| WO | WO 06/130903 | 12/2006 |
| WO | WO 06/138346 | 12/2006 |
| WO | WO 06/138416 | 12/2006 |
| WO | WO 07/006089 | 1/2007 |
| WO | WO 07/009182 | 1/2007 |
| WO | WO 07/021777 | 2/2007 |
| WO | WO 07/022562 | 3/2007 |
| WO | WO 07/041751 | 4/2007 |
| WO | WO 07/041786 | 4/2007 |
| WO | WO 07/045008 | 4/2007 |
| WO | WO 07/048174 | 5/2007 |
| WO | WO 07/053878 | 5/2007 |
| WO | WO 07/114492 | 10/2007 |
| WO | WO 07/147088 | 12/2007 |
| WO | WO 08/007985 | 1/2008 |

(56) References Cited

FOREIGN PATENT DOCUMENTS

| | | |
|---|---|---|
| WO | WO 08/011682 | 1/2008 |
| WO | WO 08/014543 | 2/2008 |
| WO | WO 08/030831 | 3/2008 |
| WO | WO 08/060295 | 5/2008 |
| WO | WO 08/068966 | 6/2008 |
| WO | WO 08/070929 | 6/2008 |
| WO | WO 08/106716 | 9/2008 |
| WO | WO 08/148086 | 12/2008 |
| WO | WO 09/026627 | 3/2009 |
| WO | WO 09/022248 | 4/2009 |
| WO | WO 09/052560 | 4/2009 |
| WO | WO 09/059353 | 5/2009 |
| WO | WO 09/092057 | 7/2009 |
| WO | WO 09/139647 | 11/2009 |
| WO | WO 10/066004 | 6/2010 |
| WO | WO 10/073142 | 7/2010 |
| WO | WO 10/131189 | 11/2010 |
| WO | WO 10/135785 | 12/2010 |
| WO | WO 11/014931 | 2/2011 |
| WO | WO 11/059346 | 5/2011 |
| WO | WO 11/060479 | 5/2011 |
| WO | WO 11/077254 | 6/2011 |
| WO | WO 12/040791 | 4/2012 |
| WO | WO 12/045127 | 4/2012 |
| WO | WO 12/052902 | 4/2012 |
| WO | WO 12/143822 | 10/2012 |
| WO | WO 14/020469 | 2/2014 |
| WO | WO 14/109749 | 7/2014 |
| WO | WO 14/175752 | 10/2014 |
| WO | WO 14/175753 | 10/2014 |
| WO | WO 15/033287 | 3/2015 |
| WO | WO 16/000040 | 1/2016 |
| WO | WO 17/049356 | 3/2017 |
| WO | WO 17/049357 | 3/2017 |
| WO | WO 18/007966 | 1/2018 |
| WO | WO 18/064712 | 4/2018 |

OTHER PUBLICATIONS

U.S. Appl. No. 60/496,059, filed Aug. 18, 2003, Ho et al.
U.S. Appl. No. 60/529,696, filed Dec. 16, 2003, Lithgow et al.
U.S. Appl. No. 61/064,406, filed Mar. 4, 2008, Wehbeh.
U.S. Appl. No. 61/071,893, filed May 22, 2008, Wehbeh et al.
U.S. Appl. No. 61/136,617, filed Sep. 19, 2008, Wehbeh et al.
Fisher & Paykel HC200 Series Nasal CPAP Blower & Heated Humidifier User Manual, 17 pp., May 1998.
Fisher & Paykel Healthcare, FlexiFit® 431 Full Face Mask instructions, 2010, 4 pp.
Fisher & Paykel Healthcare, FlexiFit™ 431 Full Face Mask, specification sheet, 2004, 2 pp.
Fisher & Paykel Healthcare, Interface Solutions Product Profile, 2006, 12 pp.
Fisher & Paykel MR810 Manual, Rev. C, 2004, 43 pp.
HomeDepot.com--Ring Nut Sales Page (Retrieved Oct. 16, 2015 from http://www.homedepot.com/p/Everbilt-1-2-in-Galvanized-HexNut-804076/20464-7893), 4 pp.
Malloy, 1994, Plastic Part Design for Injection Molding, Hanswer Gardner Publications, Inc, Cincinnati, OH, 14 pp.
Merriam-Webster's Collegiate Dictionary, Eleventh Edition, 2004, pp. 703, 905, 1074, 1184.
Philips Respironics 'System One Heated Humidifier—User Manual', 2011, pp. 1-16, [retrieved on Nov. 25, 2013] from the internet: URL: http://www.cpapxchange.com/cpap-machines-biap-machines/system-one-60-seri-es-cpap-humidifier-manual.pdf front cover, pp. 3-4 and 6.
ResMed FlexiFit brochure.
ResMed Exhibit, FlexiFit™ 431, product brochure, web pages (Wayback Machine), 2006, 23 pp.
ResMed Origins Brochure (Retrieved Apr. 17, 2016 from http://www.resmed.com/us/dam/documents/articles/resmedorigins.pdf), 64 pp.
ResMed Ultra Mirage™ Full Face Mask, product brochure, 2004, 2 pp.
ResMed Ultra Mirage™ Full Face Mask, product brochure, web pages (Wayback Machine), 2006, 9 pp.
ResMed, Jun. 29, 1997, Mask Frames (Source: Wayback Machine Internet Archive); http://web.archive.org/web/19970629053430/http://www.resmed.com-/maskframes/mask.htm, 2 pp/.
ResMed, Mirage Swift™ Nasal Pillows System from ResMed, product brochure, 2004, 6 pp.
ResMed, Mirage Swift™ Nasal Pillows System: User's Guide, product brochure, 2004, 11 pp.
ResMed, Mirage Vista™ Nasal Mask: Components Card, product brochure, 2005, 1 p.
The American Heritage Dictionary of the English Language, Fourth Edition, 2006, pp. 1501, 1502, 1650.
WeddingBands.com—Men's Wedding Ring Shopping Page (Retrieved Oct. 16, 2015 from http://www.weddingbands.com/ProductPop.sub.--wedding.sub.--band-s.sub.--metal/48214W.html), 3 pp.
Australian Examination Report in patent application No. 2012265597 dated Dec. 19, 2013, 5 pages.
Australian Examination Report in patent application No. 2015201920, dated Jul. 20, 2015, 3 pages.
Australian Examination Report in patent application No. 2007273324, dated May 22, 2012, 3 pages.
Australian Examination Report in patent application No. 2010241390, dated Jan. 9, 2015, 4 pages.
Australian Examination Report in patent application No. 2010246985, dated Mar. 4, 2014, 5 pages.
Australian Examination Report in patent application No. 2015202814, dated Aug. 14, 2015, 8 pages.
Australian Examination Report in patent application No. 2016202799, dated May 31, 2016, 2 pages.
Australian examination report in patent application No. 2016202801, dated Jun. 20, 2016, 2 pages.
Australian Examination Report in patent application No. 2016204384, dated Aug. 5, 2016, 2 pages.
Australian examination report in patent application No. 2017200991, dated Oct. 13, 2017, 3 pages.
Australian examination report in patent application No. 2017201021, dated Apr. 7, 2017, 6 pages.
Canadian Examination Report in patent application No. 2655839, dated Oct. 4, 2013, 2 pages.
Canadian Examination Report in patent application No. 2780310, dated Jul. 26, 2016, 4 pages.
Canadian Examination Report in patent application No. 2890556, dated Jan. 27, 2016, 3 pages.
Canadian Examination Report in patent application No. 2890556, dated Nov. 28, 2016, 4 pages.
Canadian Examination Report in patent application No. 2918167, dated Oct. 3, 2016, 4 pages.
Chinese Examination Report in patent application No. 2007800266164, dated Feb. 17, 2011, 5 pages.
Chinese Examination Report in patent application No. 201080028029.0, dated Mar. 27, 2014, 16 pages.
Chinese Second Office Action in patent application No. 201080028029.0, dated Jan. 19, 2015, 16 pages.
Chinese Examination Report in patent application No. 201080028029.0, dated Sep. 14, 2015, 3 pages.
Chinese Examination Report in patent application No. 201080061122.1, dated Jul. 17, 2015, 10 pages.
Chinese Examination Report in patent application No. 201080061122.1, dated Sep. 3, 2015, 10 pages.
Chinese First Office Action in patent application No. 201210080441.8, dated Mar. 24, 2014, 4 pages.
Chinese Second Office Action for Chinese Patent Application No. 201210080441.8 dated Dec. 1, 2014 in 11 pages (with English translation).
Chinese Office Action in patent application No. 201610116121.1, dated Sep. 28, 2017, 5 pages.
Chinese Third Office Action in patent application No. 201080061122.1, dated Apr. 1, 2016, 5 pages.
European Extended Search Report; dated Apr. 2, 2014; Application No. 09819444.2; 8 pages.

(56) References Cited

OTHER PUBLICATIONS

European Examination Report in patent application No. 07808683.2, dated Jul. 8, 2015, 8 pages.
European Search Report and Written Opinion dated May 12, 2016 in patent application No. 09746823.5; 11 pages.
European Examination Report in patent application No. 09746823.5, dated Apr. 3, 2017, 2 pages.
European Extended Search Report in patent application No. 10774623.2, dated Sep. 8, 2015, 7 pages.
European Extended Search Report in patent application No. 10830251.4, dated Sep. 4, 2015, 7 pages.
Great Britain Combined Search and Examination Report in patent application No. GB1406401.8, dated May 7, 2014, 4 pages.
Great Britain Combined Search and Examination Report in patent application No. GB1406402.6, dated May 7, 2014, 6 pages.
Great Britain Examination Report in patent application No. GB1119385.1, dated May 9, 2013, 4 pages.
Great Britain Search and Examination Report, in patent application No. GB1210075.6, dated Mar. 14, 2013, 2 pages.
International Search Report for application No. PCT/NZ2005/000062 dated May 27, 2005.
International Search Report for International application No. PCT/NZ2007/000185, dated Oct. 31, 2007, in 3 pages.
International Search Report, PCT/NZ2009/000072, dated Jul. 28, 2009, 4 pages.
International Search Report, International application No. PCT/NZ2009/000219, dated Feb. 2, 2010, 3 pages.
International Preliminary Report on Patentability (IPRP), International application No. PCT/NZ2009/000219, dated Apr. 12, 2011, 9 pages.
International Search Report, PCT/NZ2010/000229, dated Mar. 18, 2011, 8 pages.
International Preliminary Report on Patentability and Written Opinion of the ISA, International application No. PCT/NZ2010/000229, dated May 22, 2012, 14 pages.
Written Opinion of the International Searching Authority, PCT/NZ2010/000229, dated Mar. 18, 2011, 13 pages.
International Search Report, application No. PCT/NZ2013/000138, dated Nov. 1, 2013, 7 pages.
International Search Report for International application No. PCT/NZ2014/000021, filed Feb. 21, 2014.
Indian Office Action in Patent Application No. 5250/KOLNP/2008, dated May 23, 2017, 8 pages.
Japanese Examination Report in patent application No. 2012-510418, dated Feb. 10, 2014, 4 pages.
Japanese Examination Report in patent application No. 2012-538784, dated Aug. 25, 2014, 3 pages.
Japanese Examination Report in patent application No. 2012-538784, dated Aug. 5, 2015, 8 pages.
Japanese Examination Report in patent application No. 2012-538784, dated Jul. 25, 2016, 2 pages.
Japanese Examination Report in patent application No. 2015-098324, dated Jul. 22, 2015, 8 pages.
U.S. Appl. No. 61/064,406, 34 pages, filed Feb. 23, 2009.
U.S. Appl. No. 61/071,893, 43 pages, filed Feb. 23, 2009.
U.S. Appl. No. 61/136,617, 82 pages, filed Feb. 23, 2009.
Petition for Inter Partes Review of U.S. Pat. No. 8,479,741 Pursuant to 35 U.S.C. §§ 311-19, 37 C.F.R. § 42, IPR2016-01714, dated Sep. 7, 2016.
Patent Owner Preliminary Response to Petition for Inter Partes Review of U.S. Pat. No. 8,479,741, IPR2016-01714, filed Dec. 14, 2016.
Decision Denying Institution of Inter Partes Review of U.S. Pat. No. 8,479,741 Pursuant to 37 C.F.R. § 42.108, IPR2016-01714, entered Mar. 10, 2017.
Declaration of Dr. John Izuchukwu, Ph.D., P.E., U.S. Pat. No. 8,443,807, IPR Nos. 2016-1726 & 2016-1734, dated Sep. 7, 2016.
Declaration of Dr. John Izuchukwu, Ph.D., P.E., U.S. Pat. No. 8,479,741, IPR Nos. 2016-1714 & 2016-1718, dated Sep. 7, 2016.
Patent Owner Preliminary Response to Petition for Inter Partes Review of U.S. Pat. No. 8,479,741, IPR2016-01718, filed Dec. 16, 2016.
Decision Denying Institution of Inter Partes Review of U.S. Pat. No. 8,479,741 Pursuant to 37 C.F.R. § 42.108, IPR2016-01718, entered Mar. 13, 2017.
Petition for Inter Partes Review of U.S. Pat. No. 8,479,741 Pursuant to 35 U.S.C. §§ 311-19, 37 C.F.R. § 42, IPR2016-01718, dated Sep. 7, 2016.
Petition for Inter Partes Review of U.S. Pat. No. 8,443,807 Pursuant to 35 U.S.C. §§ 311-19, 37 C.F.R. § 42, IPR2016-01726, dated Sep. 7, 2016.
Patent Owner Preliminary Response to Petition for Inter Partes Review of U.S. Pat. No. 8,443,807, IPR2016-01726, filed Dec. 13, 2016.
Decision Denying Institution of Inter Partes Review of U.S. Pat. No. 8,443,807 Pursuant to 37 C.F.R. § 42.108, IPR2016-01726, entered Mar. 6, 2017.
Petition for Inter Partes Review of U.S. Pat. No. 8,443,807 Pursuant to 35 U.S.C. §§ 311-19, 37 C.F.R. § 42, IPR2016-01734, dated Sep. 7, 2016.
Patent Owner Preliminary Response to Petition for Inter Partes Review of U.S. Pat. No. 8,443,807, IPR2016-01734, filed Dec. 22, 2016.
Decision Denying Institution of Inter Partes Review of U.S. Pat. No. 8,443,807 Pursuant to 37 C.F.R. § 42.108, IPR2016-01734, entered Mar. 13, 2017.
File History of U.S. Pat. No. 8,479,741 to McAuley et al, published Oct. 1, 2009.
File History of U.S. Pat. No. 8,443,807 to McAuley et al, published Jan. 7, 2010.
Patent Owner's Complaint for *Fisher & Paykel Healthcare Ltd. v. ResMed Corp.*, Case No. 2:16-cv-06099-R-AJW (C.D. Cal.), dated Aug. 15, 2016.
Patent Owner's Notice of Voluntary Dismissal Without Prejudice for *Fisher & Paykel Healthcare Ltd. v. ResMed Corp.*, Case No. 2:16-cv-06099-R-AJW (C.D. Cal.), dated Aug. 16, 2016.
Patent Owner's Complaint for *Fisher & Paykel Healthcare Ltd. v. ResMed Corp.*, Case No. 3:16-cv-02068-GPC-WVG (S.D. Cal.), dated Aug. 16, 2016.
Petitioners' Complaint for *ResMed Inc., et al. v. Fisher & Paykel Healthcare Corp. Ltd., et al.*, Case No. 3:16-cv-02072-JAH-MDD (S.D. Cal.), dated Aug. 16, 2016.
Petitioners' Notice of Voluntary Dismissal Without Prejudice for *ResMed Inc., et al. v. Fisher & Paykel Healthcare Corp. Ltd., et al.*, Case No. 3:16-cv-02072-JAH-MDD (S.D. Cal.), dated Aug. 18, 2016.
Statutory Declaration made by Alistair Edwin McAuley, Apr. 9, 2015, in the matter of an Opposition by Fisher & Paykel Healthcare Limited of Australian patent application 2009221630 in the name of ResMed Limited.
Resmed Mirage Swift™ II Nasal Pillows System product page (http://www.resmed.com/en-us/products/masks/mirage_swiftII_nasalpillows.system/Mirage-Swift-II-Nasal-Pillows-System.html?menu=products); archived Jul. 21, 2008, 2 pp.
Resmed Mirage Swift™ II user brochure (http://www.resmed.com/en us/products/masks/mirage-swift_II_nasal_pillows_system/documents/mirage-swift-ii-np-brochure-patient-english-usa.pdf) copyright 2007, 4 pp.
ResMed Mirage Swift II Fitting guide (http://www;resmed.com/en-us/products/masks/mirage_swift_II_nasal_pillows_system/documents/mirage-swift_ii_np-fitting_English.pdf) copyright 2006, 2 pp.
ResMed Mirage Swift II comparison to older Swift patient interface (http://www.resmed.com/en-us/products/masks/mirage_swift_II_nasal_pillows_system/documents/mirage-swift-ii-np-comparison-guide.pdf, 2007, 6 pp.
ResMed Mirage Swift II user guide (http://www.resmed.com/en-us/products/service_and_support/documents/60893rl_mirage_swiftII_nasal_userglide_us_multi.pdf) copyright 2006, 1 p.
ResMed Mirage Swift II component card (http://www.resmed.com/en-us/products/masks/mirage_swift_II_nasal_pillows_system/documents/mirage-swift-ii-np-cc-usa.pdf); copyright 2006, 2 pp.

(56) References Cited

OTHER PUBLICATIONS

Resmed Swift™ LT Nasal Pillows System, product page, (http://www.resmed.com/en-us/products/masks/mirage_swift_II_nasal_pillows_system/Mirage-Swift-II-Nasal_Pillows-System.html?menu=products), Jul. 3, 2008, 2 pp.
Resmed Swift LT user brochure, (http://www.resmed.com/en-us/products/masks/mirage_swift_II_nasal_pillows_system/documents/mirage-swift-ii-np-brochure-patient-english-usa.pdf), copyright 2008, 4 pp.
Resmed Swift™ LT component card (http://www.resmed.com/en-us/assets/documents/product/swift_It/components_card/1012463_swift-It_components-card_usa_eng.pdf) copyright 2008, 46 pp.
Resmed Swift™ LT fitting guide, (http://www.resmed.com/en-us/assets/documents/product/swift-II/clinical_fact_sheet/1012406 swift-ii_fact-sheet_usa_eng.pdf), 2008, 2 pp.
Resmed Swift™ LT fact sheet (http://www.resmcd.com/en-us/assets/documents/product/swift-It/clinical_fact_sheet/1012406 swiftIt_fact-sheet_usa_eng.pdf, copyright 2008, 4 pp.
Resmed Swift™ LT image gallery (http://www.resmed.com/en-us/products/masks/swift_It_nasal_pillows_system/imagegallery.html?menu=products, Apr. 25, 2008, 2 pp.
Resmed Swift™ LT interactive fitting guide—screenshot from troubleshooting part (http://www.resmed.com/enus/assets/multimedia/product/swift-It/flash/swift-It-fitting-eng.swf), Jul. 3, 2008, 2 pp.
Puritan Bennett Breeze® SleepGear® CPAP Interface, product page (http:/puritanbennett.com/prod/product.aspx?id=233); archived Oct. 19, 2007, 2 pp.
Puritan Bennett Breeze® SleepGear® User's Guide (http://puritanbennett.com/_catalog/pdf/dfu/107598a00[I].pdf); copyright 2007, 18 pp.
Puritan Bennett Breeze® SleepGear® sales sheet (http://www.puritanbennett.com/_Catalog/PDF/Product/BreezeSleepGear.pdf) copyright 2016, 7 PP.
Puritan Bennett mask coding matrix (http://www.puritanbennett.com/_Cataiog/PDF/Product/BreezeSlpGear(ST03700).pdf) copyright 2006, 3 pp.
Puritan Bennett Breeze fitting guide (http://www.puritanbennett.com/_Catalog/PDF/Product/BreezeFittingPoster.pdf, Oct. 19, 2007, 1 p.
Respironics Optilife Pillows mask product page (http://optilife.respironics.com:80/); archived Nov. 21, 2007, 2 pp.
Respironics Optilife Pillows mask part numbers page (http://optilife.respironics.com:80/Parts.aspx); archived Nov. 23, 2007, 4 pp.
Respironics Optilife Pillows mask FAQ (http;//optilife.respironics.com:80/fags.aspx); archived Nov. 23, 2007, 6 pp.
Respironics Optilife Pillows mask feature page (http://optilife.respironics.com:80/features.aspx); archived Nov. 23, 2007, 4 pp.
Respironics Optilife Pillows mask fitting guide screen shot (http://optilife.respironics.com:80/fittingGuide.aspx); archived Aug. 7, 2008, 1 p.
Respironics Optilife Pillows mask adjustment video screenshots, https://www.youtube.com/watch?v=shjcNmvvcBA); uploaded Aug. 3, 2008, 2 pp.
Puritan Bennett Breeze description; copyright 2000 by Mallinckrodt Inc., 4 pp.
Fisher & Paykel Opus product page, archived Sep. 3, 2009, 2 pp.
Fisher & Paykel Opus patient interface product photographs, Jul. 2007, 6 pp.
Photographs of Opus 360 nasal pillow mask patient instructions RevB, Jul. 2007, 4 pp.
Respironics Optilife brochure detailing updates; copyright 2008; dated Mar. 26, 2008, 3 pp.
Fisher & Paykel Opus product page, archived Sep. 7, 2009, 2 pp.
Fisher & Paykel Opus "Off-the-lips" pillows explanation page, archived Aug. 23, 2009, 2 pp.
Fisher & Paykel Opus "Off-the-lips" patient interface brochure, archived Oct. 14, 2009, 6 pp.
Fisher & Paykel Opus user-guide, archived Nov. 17, 2009, 2 pp.
Australian Examination Report No. 1, in patent application No. AU 2013300237, dated Jun. 8, 2017, in 4 pages.
Australian Examination Report in patent application No. 2016238904 dated May 4, 2018, 5 pages.
Australian Examination Report in patent application No. 2010241390, dated Sep. 28, 2016, 4 pages.
Australian examination report in patent application No. 2018202409, dated Jan. 21, 2019, 4 pages.
Australian examination report in patent application No. 2018201975, dated Mar. 30, 2019, 4 pages.
Australian examination report in patent application No. 2018217307, dated Mar. 4, 2019, 4 pages.
Australian examination report in patent application No. 2018236891, dated Jun. 25, 2019, 3 pages.
Australian examination report in patent application No. 2018236891, dated Jun. 9, 2020, 3 pages.
Australian Examination Report No. 2 for patent application No. 2018217307, dated Mar. 3, 2020, 4 pp.
Australian Examination Report No. 1 in patent application No. 2019280016, dated Jul. 22, 2020.
Brazilian office action dated Jul. 11, 2019 in patent application No. BR11201211420-4.
Brazilian office action dated Aug. 28, 2020 in patent application No. PI1012207-9.
Canadian Examination Report in patent application No. 2780310, dated Jan. 25, 2018 4 pages.
Canadian Examination Report in patent application No. 2780310, dated Oct. 9, 2018, 3 pp.
Canadian Examination Report in patent application No. 2998247, dated Jan. 8, 2019, 4 pages.
Canadian Examination Report in patent application No. 3010066, dated May 3, 2019, 4 pages.
Canadian Examination Report in patent application No. 3010066, dated Dec. 19, 2019, 4 pages.
Canadian Examination Report in patent application No. 2880749, dated May 16, 2019, 5 pages.
Canadian Examination Report in patent application No. 3017161, dated Aug. 21, 2019, 3 pp.
Canadian Examination Report in patent application No. 3017161, dated Apr. 22, 2020, 4 pp.
Canadian Examination Report for patent application No. 2880749, dated Feb. 28, 2020, 5 pp.
Canadian Examination Report for patent application No. 2880749, dated Oct. 5, 2020, 4 pp.
Chinese Third Office Action in patent application No. 201610116121.1, dated Apr. 28, 2019, 16 pages.
Chinese Fourth Office Action in patent application No. 201610116121.1, dated Sep. 30, 2019, 12 pages.
Chinese Examination Report in patent application No. 201610114706.X, dated Jul. 30, 2018, 9 pp., with translation.
Chinese Second Examination Report in patent application No. 201610114706.X, dated Apr. 24, 2019 8 pp., with translation.
Chinese Third Examination Report in patent application No. 201610114706.X, dated Jan. 16, 2020, with translation.
Chinese Fourth Examination Report in patent application No. 201610114706.X, dated Aug. 28, 2020, with translation.
Chinese Examination Report dated Feb. 22, 2019 in patent application No. 201611251618.0.
Chinese First Office Action in patent application No. 201710824612.6, dated Sep. 30, 2019, 25 pp.
Chinese Second Office Action in patent application No. 201710824612.6, dated May 25, 2020.
European Examination Report in patent application No. 07808683.2, dated May 9, 2018, 3 pages.
European Summons to Attend Oral Proceedings and Written Opinion dated Dec. 13, 2017 in patent application No. 09746823.5; 7 pages.
European Examination Report, European Application 13828380.9, dated Apr. 7, 2017, 7 pp.
European Examination Report, European Application 13828380.9, dated Jul. 27, 2018, 8 pp.
European Examination Report, European Application 13828380.9, dated Mar. 3, 2020, 8 pp.
European extended search report dated Jul. 23, 2018 in patent application No. 18163847.9, 7 pp.

(56) References Cited

OTHER PUBLICATIONS

European examination report dated Sep. 5, 2019 in patent application No. 18163847.9, 5 pp.
European examination report dated Jun. 16, 2020 in patent application No. 18163847.9, 5 pp.
European extended search report dated Sep. 21, 2018 in patent application No. 18178220.2, 7 pp.
European extended search report dated Oct. 31, 2018 in patent application No. 18171619.2, 9 pp.
European Extended Search Report in patent application No. 17179765.7, dated Dec. 11, 2017.
European Extended Search Report dated Feb. 14, 2019 in patent application No. 18195537.8.
European Examination Report dated Mar. 16, 2020 in patent application No. 18195537.8.
European Search Report in patent application No. 11830981.4, dated Aug. 24, 2015, 6 pages.
European Search Report in patent application No. 191976761.1, dated Mar. 3, 2020, 10 pages.
European Extended Search Report dated Jul. 7, 2020 in patent application No. 19217524.8, 13 pp.
German examination report dated Aug. 31, 2020 in patent application No. 11 2010 011 994.0, 18 pp.
Great Britain Combined Search and Examination Report in patent application No. GB1719334.3, dated Nov. 30, 2017, in 9 pages.
Great Britain examination report dated May 30, 2018 in patent application No. GB1719334.3, 4 pp.
Great Britain examination report dated Jul. 20, 2018 in patent application No. GB1719334.3, 3 pp.
Great Britain combined search and examination report dated May 11, 2018 in patent application No. GB1805606.9, 7 pp.
Great Britain examination report dated Jul. 5, 2018 in patent application No. GB1805606.9, 3 pp.
Great Britain examination report dated May 11, 2018 in patent application No. GB1803255.7, 7 pp.
Great Britain examination report dated May 11, 2018 in patent application No. GB1805605.1, 7 pp.
Great Britain examination report in patent application No. GB1501499.6, dated Jun. 1, 2017, in 8 pages.
Great Britain Combined Search and Examination Report under Section 18(3), Application No. GB1501499.6, dated Oct. 12, 2017, in 4 pages.
Indian Examination Report received Mar. 14, 2019 in patent application No. 1431/KOLNP/2012.
Indian Examination Report received Mar. 14, 2019 in patent application No. 8767/CHENP/2011.
International Search Report, PCT/NZ2011/000211, dated Feb. 17, 2012, 4 pages.
Written Opinion, PCT/NZ2011/000211, dated Feb. 17, 2012, 7 pages.
Written Opinion of the International Searching Authority, PCT/NZ2013/000139, dated Nov. 1, 2013.
Japanese Examination Report in patent application No. 2017-040092, dated Feb. 5, 2018.
Japanese Official Action dated Sep. 3, 2018 in patent application No. 2017-238259.
Japanese examination report in patent application No. 2015-526496, dated Apr. 17, 2017, in 13 pages.
Japanese Examination Report in patent application No. 2015-526496, dated Feb. 28, 2018, 2 pp.
Japanese Decision for Final Rejection dated Jul. 1, 2019 in patent application No. 2017-238259, 2 pp.
Japanese office action dated Sep. 1, 2019 in patent application No. 2018-188040.
Japanese office action dated Jul. 1, 2020 in patent application No. 2018-188040.
Japanese Pretrial Examination Report dated Jan. 7, 2020 in patent application No. 2017-238259.
Statutory Declaration made by Alistair Edwin McAuley, Apr. 14, 2015, in the matter of an Opposition by Fisher & Paykel Healthcare Limited of Australian patent application 2009221630 in the name of ResMed Limited.
Statutory Declaration made by Alistair Edwin McAuley, Apr. 17, 2015, in the matter of an Opposition by Fisher & Paykel Healthcare Limited of Australian patent application 2009221630 in the name of ResMed Limited.
Statutory Declaration made by Alistair Edwin McAuley, Sep. 16, 2015, in the matter of an Opposition by Fisher & Paykel Healthcare Limited of Australian patent application 2009221630 in the name of ResMed Limited.
First Affidavit of Alistair Edwin McAuley, Dec. 5, 2016, in the matter of *Fisher and Paykel Healthcare Limited* v. *ResMed Limited* filed in the Federal Court of Australia.
Second Affidavit of Alistair Edwin McAuley, Dec. 21, 2016, in the matter of *Fisher and Paykel Healthcare Limited* v. *ResMed Limited* filed in the Federal Court of Australia.
Third Affidavit of Alistair Edwin McAuley, Jan. 31, 2017, in the matter of *Fisher and Paykel Healthcare Limited* v. *ResMed Limited* filed in the Federal Court of Australia, 284 pp.
Declaration of Anthony Michael Ging in IPR 2019-000172, IPR 2019-000173, IPR 2019-000177, IPR 2019-000178, dated Nov. 8, 2018, 329 pp.
McGraw-Hill Dictionary of Scientific and Technical Terms, Sixth Edition, 2003, Tube, p. 2200.
Claim Chart for AirFit P10, U.S. Pat. No. 9,333,315, dated Nov. 7, 2018, 3 pp.
Scheduling Order dated Jul. 16, 2019 in IPR2019-00180, 12 pp.
Decision to Institute dated Jul. 16, 2019 in IPR2019-00180, 34 pp.
Decision Denying Institute of Inter Partes Review dated Jul. 16, 2019 in IRP2019-00179, 32 pp.

\* cited by examiner

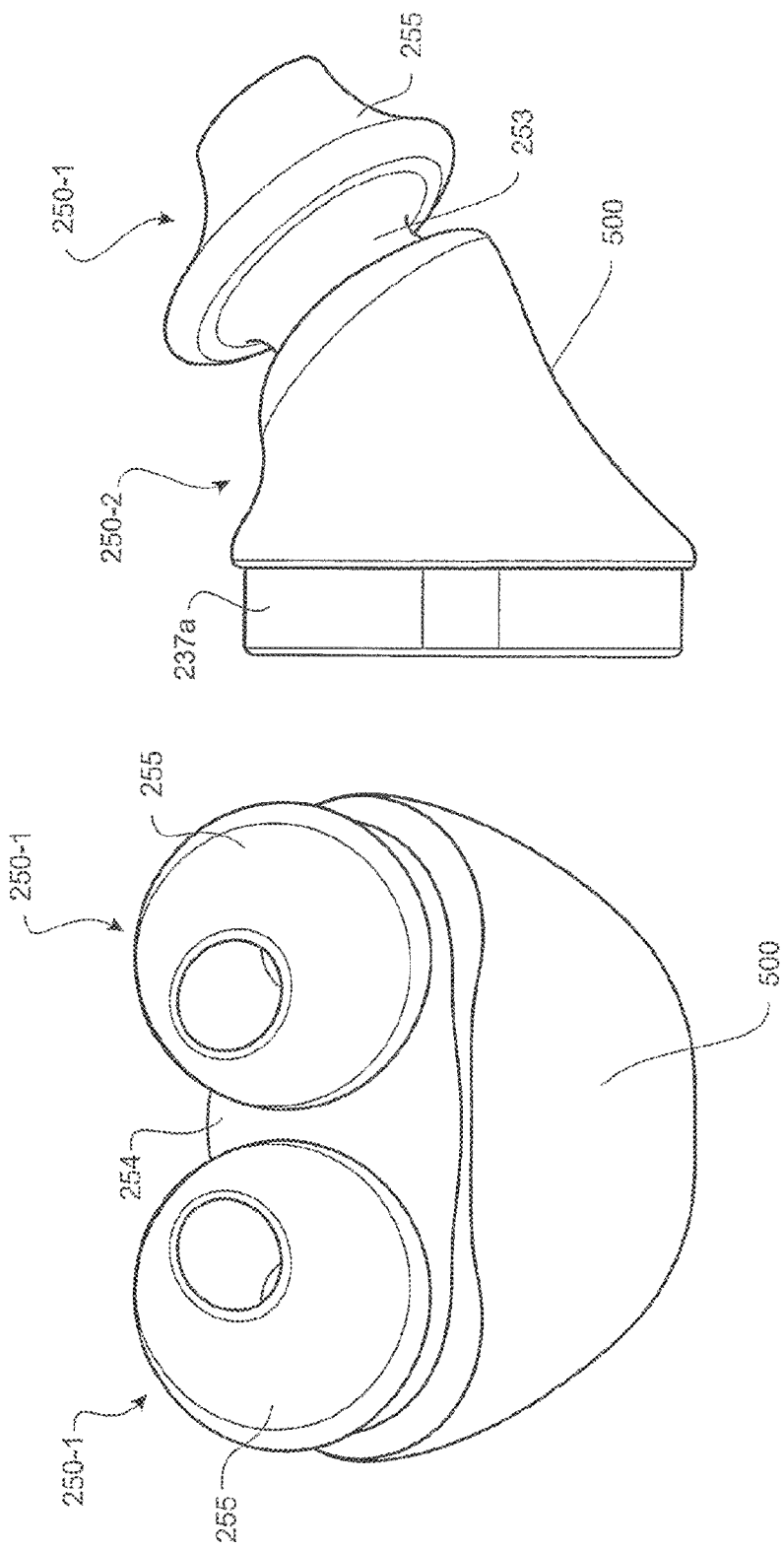

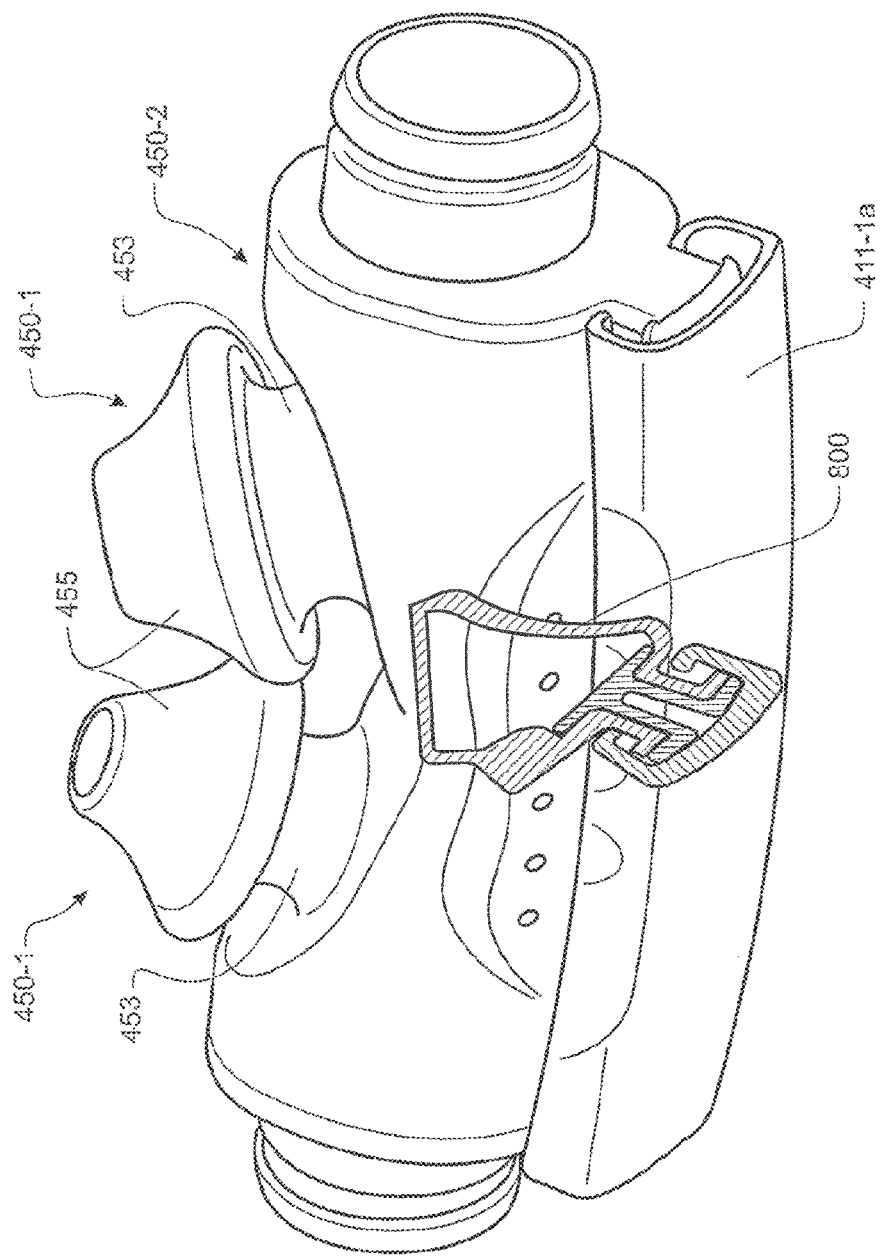

NASAL PILLOWS FOR A PATIENT INTERFACE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to nasal pillows for use with a patient interface that provides a supply of pressurised gas to a recipient via the nasal passages. The invention also relates to a patient interface which includes nasal pillows, and which may also include associated elements such as headgear. The invention also relates to a system for providing a heated, humidified stream of gases to a user via a patient interface which is included as part of the system and which includes nasal pillows.

Description of the Related Art

The prior art includes a wide variety of interfaces for supplying gases to a recipient. The following are examples.

The prior art includes a nasal mask that can be used for supplying gases to a recipient. The nasal mask includes a perimeter seal that seals across, down each cheek alongside the nose and along the surface of the upper lip. The entire enclosed space is pressurised and the recipient may inhale the pressurised gas from the enclosed space. An example is the Flexifit 405 nasal mask sold by Fisher & Paykel Healthcare.

The prior art also includes a full face mask. The full face mask includes a perimeter seal that extends across the bridge of the nose downward along each cheek beside the nose to the jaw and along the jaw below the lower lip. The perimeter thereby encloses both the nose and mouth. The entire space within the mask frame is pressurised. The recipient may breathe the pressurised gas from the space through either the nose or mouth. An example is the Flexifit 431 interface sold by Fisher & Paykel Healthcare.

The prior art further includes an oral interface including an oral appliance that fits within the user's mouth. An example is the Fisher & Paykel Healthcare Oracle interface.

The prior art still further includes a nasal pillows interface in which headgear retains a soft plenum in the vicinity of the user's nose. A pair of flexible protrusions engage against the nares of the recipient. Typically, the protrusions are able to axially compress and have a lateral freedom of movement relative to the supporting cushion. Examples are the ResMed Mirage Swift™ II, the ResMed Swift LT, or the Fisher and Paykel Opus™ 360. A variety of different pillow configurations which could be used with these interfaces are described and shown in WO 2008/014543.

The prior art still further includes a nasal cannula interface. The nasal cannula interface includes a plenum portion that rests against the upper lip of the user and a pair of prongs. Each prong extends into the nostril of the user. An example is the Nasal-Aire interface made by Innomed, where gases are provided to the interface and the prongs by conduits or hoses that extend from the users nose across their cheeks, over their ears and around the back of their head.

Interfaces such as these are frequently used for delivering pressurised gases to a person being treated for obstructive sleep apnea (OSA) or other sleep disorders. These users typically wear the interface in a home sleeping environment. Comfort and effective sealing even under conditions of patient movement are major considerations.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

SUMMARY OF THE INVENTION

It is an object of the present invention to provide an interface that goes some way towards overcoming the disadvantages of the prior art such as the devices described above, or which at least provides users with a useful choice.

In a first aspect the invention may broadly be said to consist in a nasal pillow section for use as part of an apparatus for providing a stream of gases to a user, said pillow section in use located in front of the upper lip and below the nostrils of a user, said pillow section comprising:
- a pillow gasket, having a gases aperture which receives a stream of gases in use,
- nasal pillows, fluidically connected to said pillow gasket and adapted to substantially seal against the nostrils of a user in use, so that substantially the whole of said stream of gases passes into said nasal pillows from said pillow gasket and is delivered to said user,
- the lower inner surface of said pillow gasket shaped so that in use contact between the upper lip of a user and said pillow gasket is minimised.

Preferably said lower inner surface in said first aspect is shaped as a concavity.

Preferably said pillow gasket in said first aspect includes an open lower front portion that acts as said gases aperture, and said concavity runs generally between the base or bases of said nasal pillows, and the lower rear part of said open lower front portion.

Preferably the inwards curve of the concavity for said lower inner surface in said first aspect is 3 mm from the lower edge to the upper edge.

Preferably said lower inner surface in said first aspect preferably has a width of between 30 and 50 mm and most preferably 40 mm.

Preferably the height of said lower inner surface between the outer side of said pillows and the lower rear part of said open lower front portion wall in said first aspect is preferably between 20 mm and 30 mm and most preferably between 25 mm and 27 mm.

Preferably the height of said lower inner surface between the inner side of said pillows, and the lower rear part of said open lower front portion wall in said first aspect is preferably between 20 mm and 30 mm and less than the height of said lower inner surface between the outer side of said pillows and the lower rear part of said open lower front portion wall and most preferably between 23 mm and 25 mm.

Alternatively said lower inner surface in said first aspect is a substantially straight forward-sloping planar surface.

Preferably said pillow gasket in said first aspect includes an open lower front portion that acts as said gases aperture, and said substantially straight forward-sloping planar surface runs generally between the base or bases of said nasal pillows, and the lower rear part of said open lower front portion.

Alternatively said lower inner surface in said first aspect is slightly convex.

Preferably said pillow gasket includes an open lower front portion that acts as said gases aperture, and said slightly convex lower inner surface runs generally between the base or bases of said nasal pillows, and the lower rear part of said open lower front portion, said surface deviating 3 min or less from a straight line running between the base or bases of said nasal pillows, and the lower rear part of said open lower front portion.

In a second aspect the invention may broadly be said to consist in a nasal pillow section for use as part of an apparatus for providing a stream of gases to a user, said pillow section in use located in front of the upper lip and below the nostrils of a user, said pillow section comprising:
 a pillow gasket, having a gases aperture which receives a stream of gases in use,
 nasal pillows, fluidically connected to said pillow gasket and adapted to substantially seal against the nostrils of a user in use, so that substantially the whole of said stream of gases passes into said nasal pillows from said pillow gasket and is delivered to said user,
 the lower inner surface of said pillow gasket shaped to include a concavity.

Preferably said nasal pillow section in said second aspect includes an open lower front portion that acts as said gases aperture, and said concavity runs generally between the base or bases of said nasal pillows, and the lower rear part of said open lower front portion.

Preferably the inwards curve of the concavity for said lower inner surface in said second aspect is 3 mm from the lower edge to the upper edge.

Preferably said lower inner surface in said second aspect preferably has a width of between 30 and 50 mm and most preferably 40 mm.

Preferably the height of said lower inner surface between the outer side of said pillows and the lower rear part of said open lower front portion wall in said second aspect is preferably between 20 mm and 30 mm and most preferably between 25 mm and 27 mm.

Preferably the height of said lower inner surface between the inner side of said pillows, and the lower rear part of said open lower front portion wall in said second aspect is preferably between 20 mm and 30 mm and less than the height of said lower inner surface between the outer side of said pillows and the lower rear part of said open lower front portion wall and most preferably between 23 mm and 25 mm In a third aspect the invention may broadly be said to consist in a nasal pillow section for use as part of an apparatus for providing a stream of gases to a user, said pillow section in use located in front of the upper lip and below the nostrils of a user, comprising:
 a pillow gasket, having an open lower front portion which acts as a gases aperture and which receives a stream of gases in use,
 nasal pillows, fluidically connected to said pillow gasket and adapted to substantially seal against the nostrils of a user in use, so that substantially the whole of said stream of gases passes into said nasal pillows from said pillow gasket and is delivered to said user,
 the lower inner surface of said pillow gasket formed as a substantially straight planar surface having an inner upper edge located substantially at the base of said pillows and a lower outer edge located substantially close to the lowest point of said open lower front portion.

In a fourth aspect the invention may broadly be said to consist in a nasal pillow section for use as part of an apparatus for providing a stream of gases to a user, said pillow section in use located in front of the upper lip and below the nostrils of a user, said pillow section comprising:
 a pillow gasket, having a gases aperture which receives a stream of gases in use,
 nasal pillows, fluidically connected to said pillow gasket and adapted to substantially seal against the nostrils of a user in use, so that substantially the whole of said stream of gases passes into said nasal pillows from said pillow gasket and is delivered to said user,
 the lower inner surface of said pillow gasket shaped to be slightly convex.

Preferably said pillow gasket in said fourth aspect includes an open lower front portion that acts as said gases aperture, and said slightly convex lower inner surface runs generally between the base or bases of said nasal pillows, and the lower rear part of said open lower front portion, said surface deviating 3 mm or less from a straight line running between the base or bases of said nasal pillows, and the lower rear part of said open lower front portion.

In a fifth aspect the invention may broadly be said to consist in an interface for use as part of an apparatus for providing a stream of gases to a user, comprising:
 a manifold section, including a gases supply aperture that in use receives a stream of gases, said manifold section adapted for connection to a headgear assembly so that in use said interface is held in position on the face of a user,
 a nasal pillow section including a pillow gasket and nasal pillows, said pillow gasket fluidically connected to said manifold section so that said stream of gases passes through said nasal pillow section in use, said nasal pillows adapted to substantially seal against the nostrils of a user in use, so that substantially the whole of said stream of gases is delivered to said user, said pillow section in use located in front of the upper lip and below the nostrils of a user,
 the lower inner surface of said pillow gasket shaped so that in use contact between the upper lip of a user and said pillow gasket is minimised.

Preferably said lower inner surface in said fifth aspect is shaped as a concavity.

Preferably said pillow gasket in said fifth aspect includes an open lower front portion that acts as a gases aperture and which is fluidically connected to said manifold section, and said concavity runs generally between the base or bases of said nasal pillows, and the lower rear part of said open lower front portion.

Preferably the inwards curve of the concavity for said lower inner surface in said fifth aspect is 3 mm from the lower edge to the upper edge.

Preferably said lower inner surface in said fifth aspect preferably has a width of between 30 and 50 mm and most preferably 40 mm.

Preferably the height of said lower inner surface between the outer side of said pillows and the lower rear part of said open lower front portion wall in said fifth aspect is preferably between 20 mm and 30 mm and most preferably between 25 mm and 27 mm.

Preferably the height of said lower inner surface between the inner side of said pillows, and the lower rear part of said open lower front portion wall in said fifth aspect is preferably between 20 mm and 30 mm and less than the height of said lower inner surface between the outer side of said pillows and the lower rear part of said open lower front portion wall and most preferably between 23 mm and 25 mm.

Alternatively said lower inner surface in said fifth aspect is a substantially straight forward-sloping planar surface.

Preferably said pillow gasket in said fifth aspect includes an open lower front portion that acts as a gases aperture and which is fluidically connected to said manifold section, and said substantially straight forward-sloping planar surface runs generally between the base or bases of said nasal pillows, and the lower rear part of said open lower front portion.

Alternatively said lower inner surface in said fifth aspect is slightly convex.

Preferably said pillow gasket in said fifth aspect includes an open lower front portion that acts as a gases aperture and which is fluidically connected to said manifold section, and said slightly convex lower inner surface runs generally between the base or bases of said nasal pillows, and the lower rear part of said open lower front portion, said convex surface deviating 3 mm or less from a straight line running between the base or bases of said nasal pillows, and the lower rear part of said open lower front portion.

In a sixth aspect the invention may broadly be said to consist in an interface for use as part of an apparatus for providing a stream of gases to a user, comprising:
  a manifold section, including a gases supply aperture that in use receives a stream of gases, said manifold section adapted for connection to a headgear assembly so that in use said interface is held in position on the face of a user,
  a nasal pillow section including a pillow gasket and pillows, said pillow gasket fluidically connected to said manifold section so that said stream of gases passes through said nasal pillow section in use, said nasal pillows adapted to substantially seal against the nostrils of a user in use, so that substantially the whole of said stream of gases is delivered to said user, said pillow section in use located in front of the upper lip and below the nostrils of a user, the lower inner surface of said pillow gasket directly in front of said upper lip in use,
  the lower inner surface of said pillow gasket shaped to include a concavity.

Preferably said pillow gasket in said sixth aspect includes an open lower front portion that acts as a gases aperture and which is fluidically connected to said manifold section, and said concavity runs generally between the base or bases of said nasal pillows, and the lower rear part of said open lower front portion.

Preferably the inwards curve of the concavity for said lower inner surface in said fifth aspect is 3 mm from the lower edge to the upper edge.

Preferably said lower inner surface in said sixth aspect preferably has a width of between 30 and 50 mm and most preferably 40 mm.

Preferably the height of said lower inner surface between the outer side of said pillows and the lower rear part of said open lower front portion wall in said sixth aspect is preferably between 20 mm and 30 mm and most preferably between 25 mm and 27 mm.

Preferably the height of said lower inner surface between the inner side of said pillows, and the lower rear part of said open lower front portion wall in said sixth aspect is preferably between 20 mm and 30 mm and less than the height of said lower inner surface between the outer side of said pillows and the lower rear part of said open lower front portion wall and most preferably between 23 mm and 25 mm.

In a seventh aspect the invention may broadly be said to consist in an interface for use as part of an apparatus for providing a stream of gases to a user, comprising:
  a manifold section, including a gases supply aperture that in use receives a stream of gases, said manifold section adapted for connection to a headgear assembly so that in use said interface is held in position on the face of a user,
  a nasal pillow section including a pillow gasket and pillows, said pillow gasket fluidically connected to said manifold section so that said stream of gases passes through said nasal pillow section in use, said nasal pillows adapted to substantially seal against the nostrils of a user in use, so that substantially the whole of said stream of gases is delivered to said user, said pillow section in use located in front of the upper lip and below the nostrils of a user, the lower inner surface of said pillow gasket directly in front of said upper lip in use,
  the lower inner surface of said pillow gasket formed as a substantially straight planar surface having an inner upper edge located substantially at the base of said pillows and a lower outer edge located substantially close to the lowest point of said gases supply aperture.

In an eighth aspect the invention may broadly be said to consist in an interface for use as part of an apparatus for providing a stream of gases to a user, comprising:
  a manifold section, including a gases supply aperture that in use receives a stream of gases, said manifold section adapted for connection to a headgear assembly so that in use said interface is held in position on the face of a user,
  a nasal pillow section including a pillow gasket and pillows, said pillow gasket fluidically connected to said manifold section so that said stream of gases passes through said nasal pillow section in use, said nasal pillows adapted to substantially seal against the nostrils of a user in use, so that substantially the whole of said stream of gases is delivered to said user, said pillow section in use located in front of the upper lip and below the nostrils of a user, the lower inner surface of said pillow gasket directly in front of said upper lip in use,
  the lower inner surface of said pillow gasket shaped to be slightly convex.

Preferably said pillow gasket in said eighth aspect includes an open lower front portion that acts as a gases aperture and which is fluidically connected to said manifold section, and said slightly convex lower inner surface runs generally between the base or bases of said nasal pillows, and the lower rear part of said open lower front portion, said surface deviating 3 mm or less from a straight line running between the base or bases of said nasal pillows, and the lower rear part of said open lower front portion.

In a ninth aspect the invention may broadly be said to consist in a system for providing a heated, humidified stream of gases to a user, comprising:

a blower unit having a blower outlet and adapted to supply a stream of gases at a pressure above atmospheric from said blower outlet, a humidifier unit having a humidifier inlet and a humidifier outlet, said humidifier inlet fluidically connected to said blower outlet, said humidifier unit in use receiving said stream of gases and heating and humidifying said stream of gases, before passing said gases out of said humidifier outlet, an interface including a gases supply aperture, a supply conduit, one end of said supply conduit fluidically connected to said humidifier outlet to receive said stream of heated humidified gases, the other end of said supply conduit fluidically connected to said gases supply aperture to provide said stream of heated humidified gases to said interface, a headgear assembly, said interface and said headgear assembly mutually adapted to connect together and hold said interface in position on the head of a user in use, said interface as described in any one of the statements relating to the fifth to eighth aspects above.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which:

FIG. 2b shows the interface of FIG. 2a in use, being worn by a user, viewed from the same angle as FIG. 2a.

FIG. 3b shows the functionality of the connection between the supply conduit and the interface core section of the second preferred embodiment of FIG. 3a.

FIG. 3c shows a close-up view of the interface core portion or core section of FIG. 3a.

FIG. 4b shows an exploded perspective view from the front and to one side of the interface assembly of FIG. 4a.

FIG. 5a shows a first preferred form of nasal pillow section for use as part of either of the first or second preferred embodiments of interface assembly as shown in FIG. 2 or 3, the nasal pillow section having a nasal pillow gasket section and nasal pillows connected to the nasal pillow gasket section, the nasal pillow section shown being viewed from the rear looking forwards.

FIG. 5b shows the nasal pillow section of FIG. 5a, viewed from a user's right hand side if the nasal pillow section was in use as part of an interface being worn by a user.

FIG. 8b shows a perspective view from the front and to one side of the fourth preferred form of nasal pillow section of FIG. 8a, partially cut-away or transparent so that the outline of the wall and internal structure of the nasal pillow section can be seen.

FIG. 8c shows a side view of a modification of the fourth preferred form of nasal pillow section shown in FIG. 8a.

FIG. 8d shows a side view of another modification of the fourth preferred form of nasal pillow section shown in FIG. 8a.

DETAILED DESCRIPTION OF THE PREFERRED EMBODIMENT

The present invention provides an interface for use as part of an apparatus for providing a stream of gases to a patient. The preferred and alternative embodiments are for use as part of an apparatus for providing a stream of heated, humidified gases at a pressure above atmospheric pressure to a user for the purposes of CPAP therapy or similar. However, it should be noted that the interface is not limited for use as part of an apparatus for providing CPAP therapy—the interface could also be used for Bi-PAP or variable pressure therapy, as part of an apparatus used for an anti-snoring treatment regime, for the treatment of COPD, or as part of any therapy regime where a stream of gases at a pressure greater than atmospheric is delivered to the breathing passages of a patient or user via an interface assembly.

The preferred embodiment will now be described in detail with reference to the Figures. However, it should be noted that many variations are possible which have not been specifically described, without departing from the intended scope of the present invention.

Gases Supply System

Figure 1:
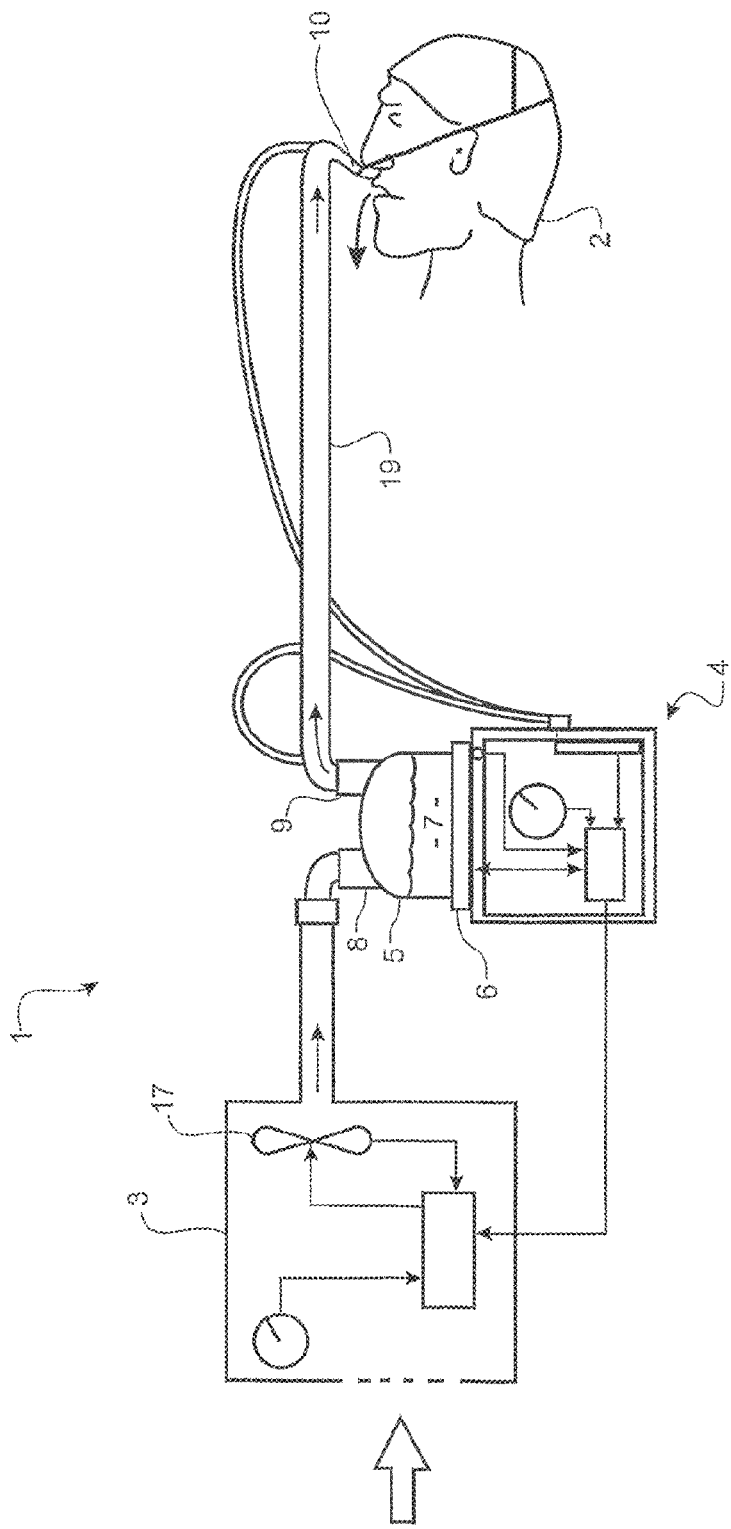
FIG. 1 shows a schematic view of a system for supplying a stream of heated humidified gases to a user via an interface assembly, the system including a gases supply unit or blower, a humidifier chamber, and a supply conduit connecting the humidifier chamber and the interface assembly.

FIG. 1 shows a schematic view of a typical system 1 for providing a stream of heated humidified gases at a pressure above atmospheric to a user 2. The system 1 includes a gases supply unit or blower unit 3 which in use receives gases from atmosphere and passes these through a fan unit 17 or similar inside the blower unit so that when the gases leave the blower unit 3, they are at a pressure above atmospheric, and are flowing at a certain flow rate. A humidifier unit 4 is located downstream from the blower unit 3, and in use receives the flow of pressurised gases from the blower unit 3. The humidifier unit 4 includes a water chamber 5 which in use contains a volume of water 7. The volume of water 7 in the chamber 5 is in use heated—in the embodiment shown in FIG. 1, the water 7 is heated by a heater plate 6 located underneath the chamber 5. The gases from the blower unit 3 pass into the chamber 5 via an entry port 8, the gases passing through the chamber 5 and across the surface of the water 7, becoming heated and humidified as they do so. The gases then pass out of the humidifier chamber 5 via a humidifier outlet port 9. It should be noted that there are many different ways in which the gases could be heated and humidified aside from the specific way described above, and any of these different ways are suitable for use as part of the system that uses the pillows of the present invention.

It should also be noted that a modular system has been described above—that is, a system where the humidifier unit 4 is a separate unit to the blower unit 3. An integrated system could also be used—that is, a system where the blower unit and the humidifier unit are two integral parts of a single unit, or where the blower unit and the humidifier unit are rigidly attached or connected together in use.

Figure 2A:
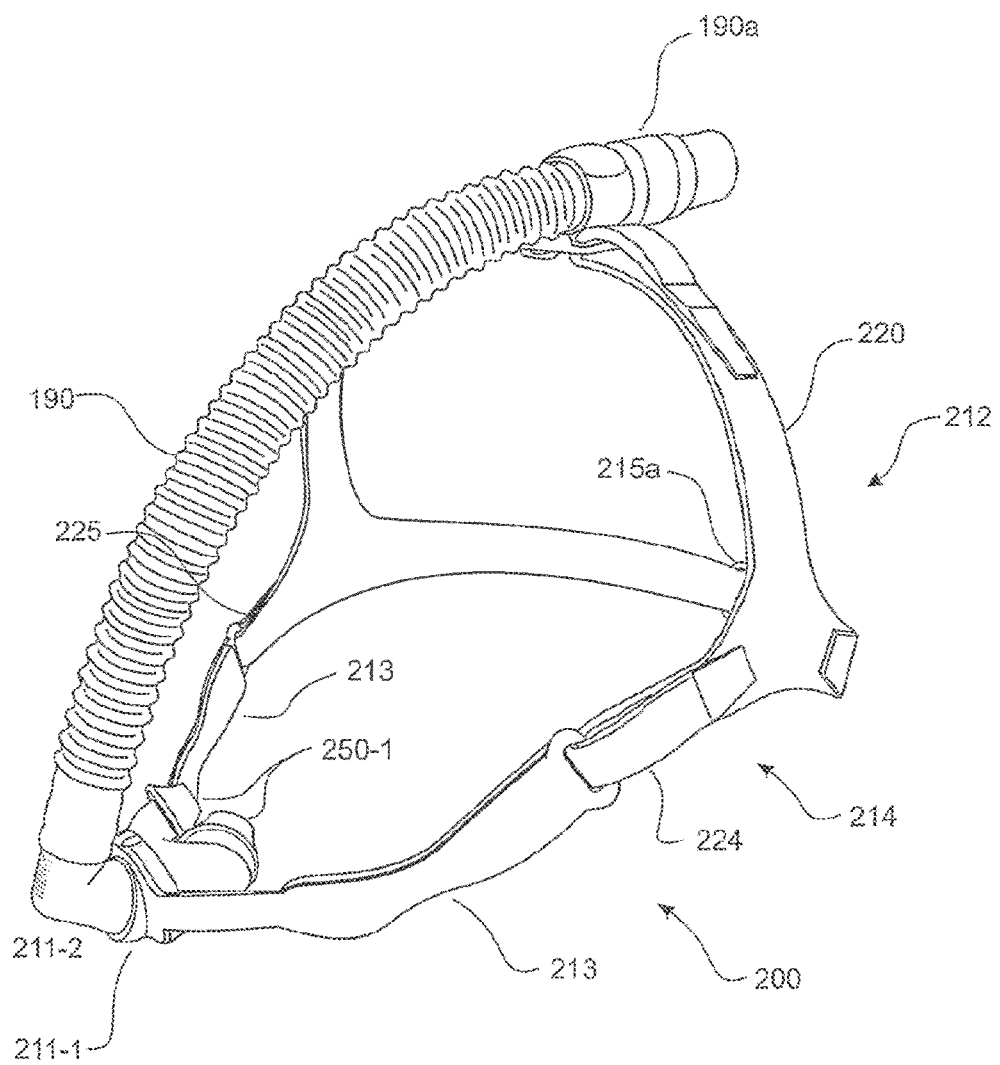
FIG. 2a shows a perspective view from the front and to one side of a first preferred embodiment of the interface assembly of the present invention, showing an interface core portion or core section adapted to connect to the supply conduit so the interface can receive gases from the gases supply unit in use, a nasal pillow section included as part of the interface core section, and a headgear assembly connected to the core section which is adapted to hold the interface in position on the head of a user.
Figure 2B:
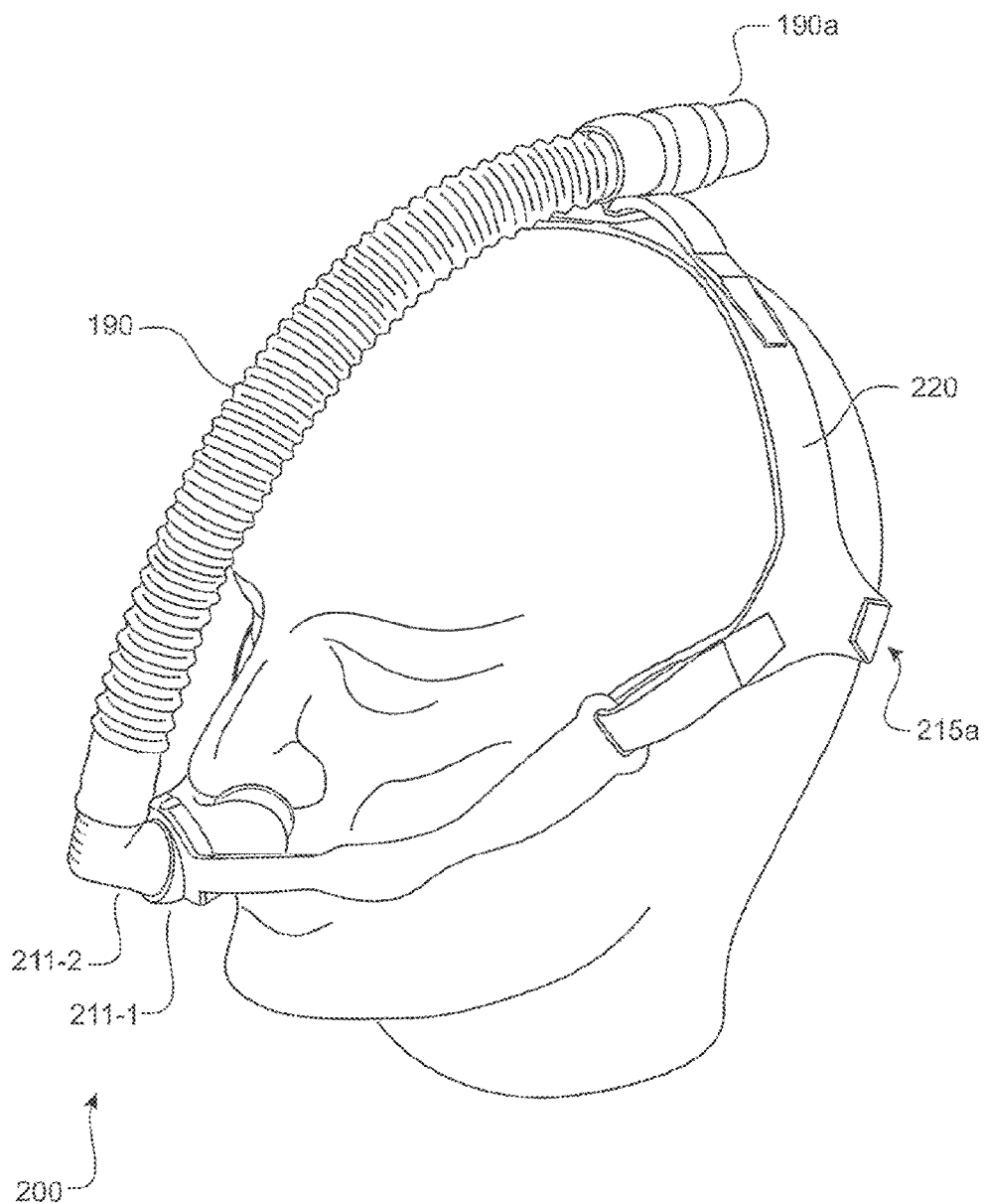
Figure 2C:
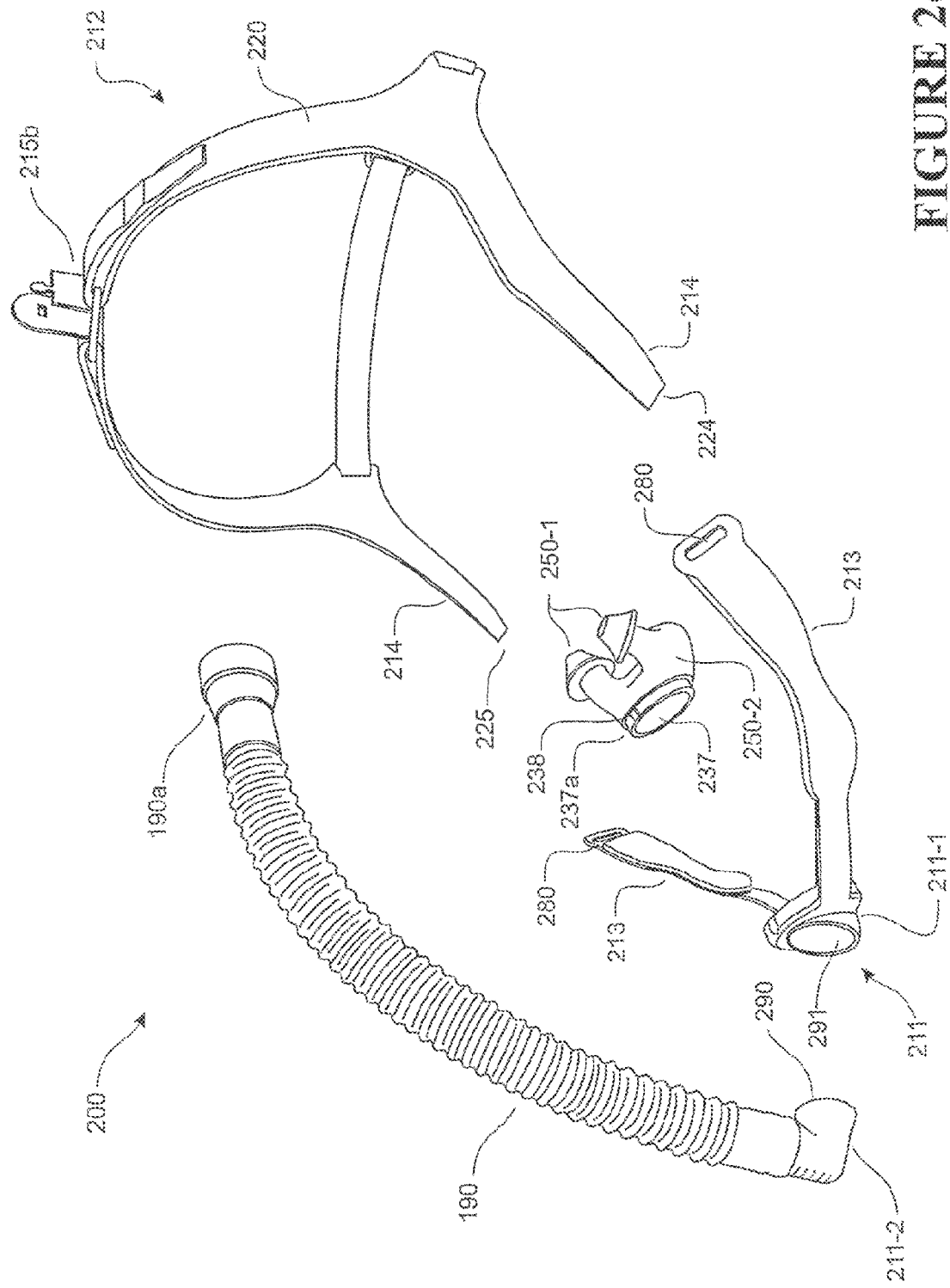
FIG. 2c shows an exploded view of the interface of FIG. 2a or 2c.
Figure 3A:
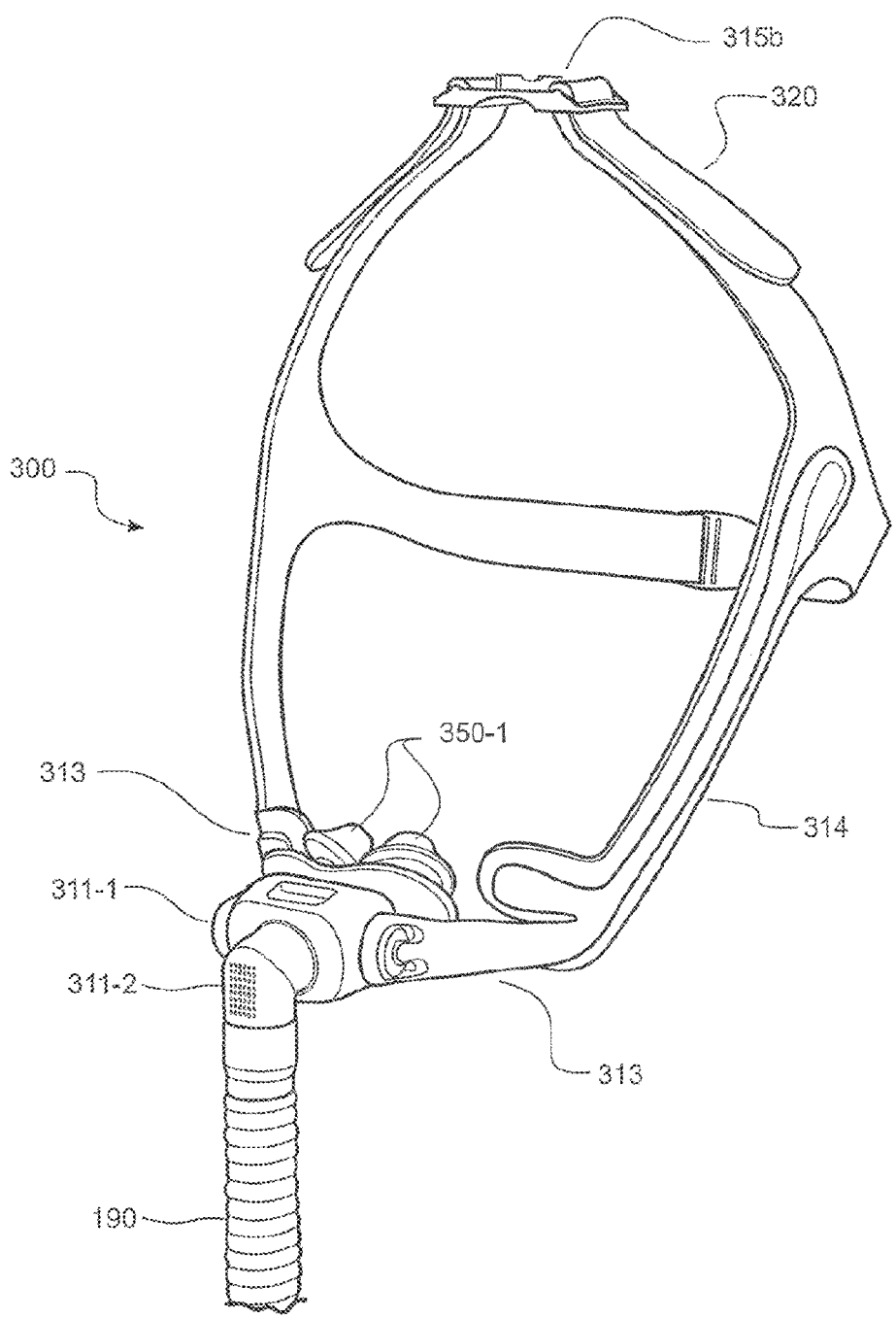
FIG. 3a shows a second preferred embodiment of the interface assembly of the present invention, the second preferred embodiment containing similar elements to those of the first preferred form of FIG. 2 but configured slightly differently.
Figure 3B:
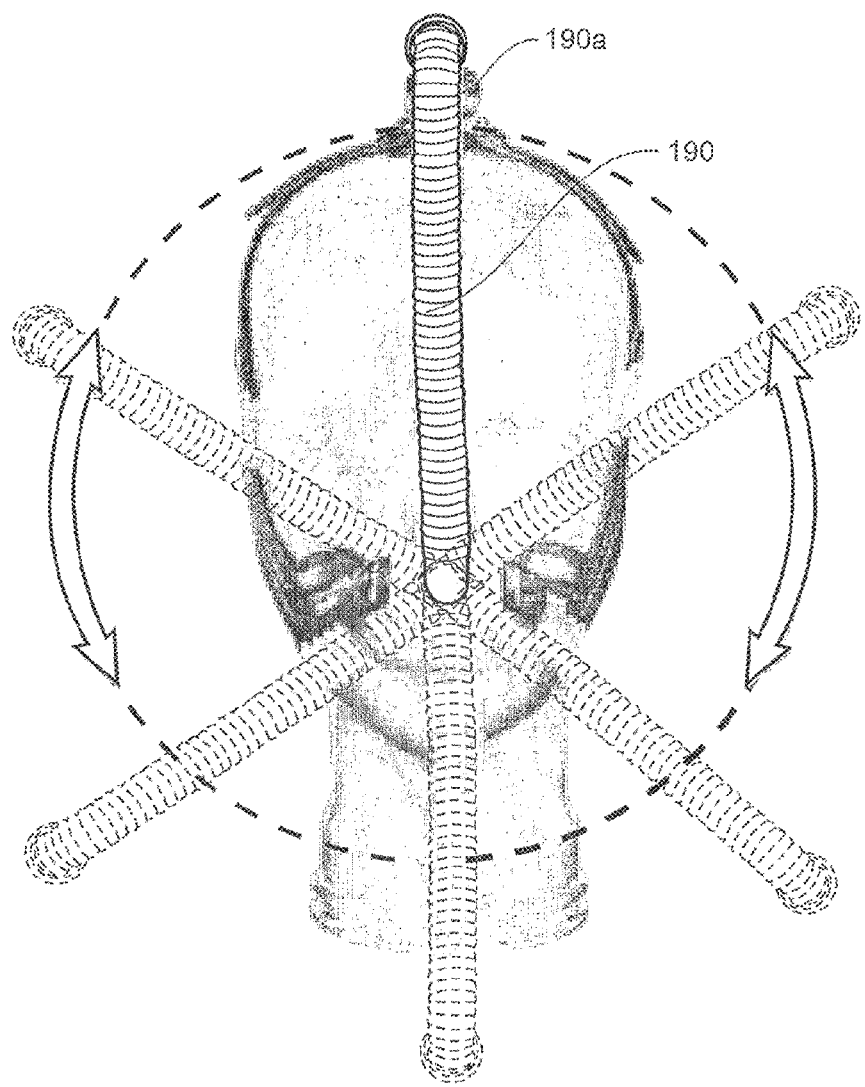

In use, one end of a main supply conduit 19 is connected to the humidifier outlet 9. The heated and humidified gases stream exits the humidifier unit 4 via the humidifier outlet 9 and enters the main supply conduit 19, passing along the supply conduit 19 to an interface assembly 10 which is connected to the user end of the supply conduit 19. The supply conduit 19 can either be directly connected to the interface assembly 10, as shown in FIG. 1, or an intervening interface conduit 190 can be used to connect between the main supply conduit 19 and the interface assembly 10, as shown in the embodiments of FIGS. 2, 3 and 4. Where the supply conduit 19 is referred to below, this should be taken to mean either the supply conduit 19 by itself, or alternatively as referring to the supply conduit in combination with the interface conduit 190.

Supply Conduit and Interface Conduit

In the preferred embodiment, the supply conduit 19 is a flexible tube formed from a plastic type material, many different variations of which are known in the art. One end of the supply conduit 19 is connected to the humidifier outlet port 9, with the other end connected either directly to the interface assembly 10, or connected to the distal end 190*a* of the interface conduit 190, the interface conduit 190 connected to the interface core section 11. The most preferred form of interface conduit 190 is approximately 30 cm or 1 foot in length, with an external diameter of between 1-2 cm and a thin ribbed wall, the ribs being approximately 2-3 mm thick and the wall between the ribs being significantly less than 1 mm thick. However, it should be noted that variations from these dimensions are possible without departing from the scope of the invention, and for example a non-ribbed conduit could be used if required. It should further be noted that 'flexible tube' as it is used in this specification should be taken to mean that the tube or conduit is flexible enough so that it is capable of being bent or deformed repeatedly (for example, by bringing the two ends of the conduit together, or by tying a loose knot in the conduit if it is long enough—e.g. approximately 30 cm or more in length), with the tube or conduit returning to its original undeformed shape with little to no plastic deformation occurring, every single time the tube or conduit is bent or deformed in this manner.

In the most preferred form, neither of the supply conduit 19 or the interface conduit 190 will rigidly support their own weight when held at one end so that the main body of the conduit extends outwards generally horizontally from the held end. Over a 20-30 cm length of supply conduit (which has a diameter of 1-2 cm and a wall thickness at the ribs of 1-3 mm and a wall thickness between the ribs of less than 1 mm), the unsupported end of the interface conduit will bend to face substantially directly downwards. For example, the interface conduit of the Swift LT™ is formed in such a manner that over a 20-30 cm length, the unsupported end will bend downwards so that it points substantially vertically downwards. The interface conduit used in the Opus is somewhat stiffer, but will still bend through an angle of very approximately 45 degrees. Both of these conduits are flexible for the purposes of this specification, and should not be thought of as 'rigid' or 'semi-rigid' (see Lexicon section for more details). The main supply conduit 19 is of similar flexibility to both of these items, but is generally slightly less flexible.

The conduits 19, 190 connect to each other, or to the interface assembly 10, or both, by a friction push fit, a bayonet connection or similar, or by any other suitable connection as might be known in the art.

Interface Assembly

Specific preferred forms of an interface assembly are shown in FIGS. 2, 3, and 4 as interface assembly 200, interface assembly 300 or interface assembly 400. The interface assemblies 200, 300, 400 have a number of common elements and differences as will be described below. In the description below, the element numbering conforms to the following convention: For the embodiment of FIG. 2, the elements unique to that embodiment will be numbered e.g. 201, 210, etc. The equivalent unique elements on the embodiments shown in FIGS. 3 and 4 will be numbered e.g. 301, 310 and 401, 410 respectively. If the element is being referred to in a general sense, it will be referred to as e.g. 1, 10 etc to show that the description is applicable to all the embodiments shown in FIGS. 2, 3, 4, and could also be applied as a general description to other, general, embodiments not specifically shown.

The interface assembly (e.g. assemblies 200, 300, 400) are assembled from two main parts: an interface core portion or interface core section 11, and a headgear assembly 12.

The interface core section 11 and the supply conduit 19 (either including or excluding the interface conduit 190) are mutually adapted so that one end (the patient end or proximal end) of the supply conduit 19 is fluidically or gaseously connected to the interface core section 11 in use, the interface core section 11 adapted so that the supply of heated, humidified gases is provided to the interior of the interface core portion 11 from the supply conduit 19 via this connection. The preferred forms of this connection will be described in detail below.

Headgear Assembly

The headgear assembly 12 is formed from two main items: a set of arms 13 that extend in use one from each side of the interface core portion 11, and a set of headgear straps 14. In the preferred embodiments, the arms 13 are formed from either a flexible or a semi-rigid plastic, backed with neoprene, foam, or similar to form a cushion portion, the cushion portion resting against the face of a user in use.

The arms 13 can be connected to the interface core portion 11 in a number of ways. For example, arms 213 could be integrally formed or integrally connected with the interface core portion 211, as shown in the embodiment of FIG. 2—the arms 213 are formed as part of the interface core portion 211. Alternatively, the arms, such as arms 313, could be removably or releasably connected to the interface core portion 311 as shown in the embodiment of FIG. 3a. In the specific embodiment of FIG. 3a, the releasable connection is made in such a manner as to allow the arms 313 to be rotatably adjusted with respect to the interface core portion 311. The embodiment of FIG. 3a with the adjustable arms shows an interface assembly 300 that has an interface core portion 311 and arms 313. The interface ends of the arms 313 are rotatably connected to the interface core portion 311 by way of a 'rotating barrel' connection as is used on the ResMed Swift™ LT, which allows the arms 313 to rotate relative to the interface core portion 311, and still remain connected. The mutual connection is formed so that when the connection is made, the arm 313 will remain in the position to which a user has rotated it—the arm 313 will not freely rotate unless manipulated by an external force.

For all of the preferred forms, the headgear straps 14 extend around the rear, or over the top of a user's head (or both) in use, to support the interface assembly 10 in position in use. In the embodiment of FIG. 2, the ends of the arms 213 in use co-locate with the ends of the headgear straps 214, with the ends of the arms 213 and the ends of the headgear straps 214 mutually adapted to connect together in use to hold the interface assembly 200 in position. In this form, the ends of the main strap 214 include two patches of Velcro™ on the outer surface at each end—one 'hook' patch and one 'loop' patch. When each of the ends is doubled back on itself to form a loop, the Velcro™ patches engage to hold this loop together. In use, the ends 224, 225 are passed one each through slots 280 on the ends of the arms 213 and then doubled back on themselves to engage the headgear assembly 212 with the core section 211. This arrangement could be used on other embodiments if required.

In alternative embodiments, such as those shown in FIGS. 3 and 4, the headgear straps 314, 414 could be formed as an extension of the cushion portion, with the headgear straps 314, 414 formed from neoprene or similar. For example, in the embodiment shown in FIG. 3, the headgear straps 314 are a single-piece item with the arms 313.

It is preferred that all the different embodiments of headgear straps 13 include a secondary upper strap 20 which passes across the top of a user's head, as well as the main strap 14 which passes behind the user's head. The secondary upper strap 20 is arranged so that it passes across the top of a users head, with each end of the secondary strap 20 connecting to the main strap 14 just behind the ears of a user. Each of these straps 14, 20 includes an adjustment mechanism such as buckles 15a, 15b or similar. These could be Velcro™ adjusters or buckles as preferred. The headgear secondary upper strap 20 could also be independently formed and connected to the main strap 14. The adjustments could be at any location on the strap that is convenient—sides, front or rear. The straps 14, 20 could be of different widths or thicknesses as required for user comfort. For example, in the most preferred form, the main strap 14 is wider than the secondary strap 20.

Suitable strap materials may include a woven elastic strip or a narrow strip of foam and fabric, such as Breathoprene™. Alternatively, the headgear could be formed from silicone, or coated with silicone. The headgear arms could be padded or cushioned on their inside surfaces if they are formed from silicone, in order to increase user comfort. Padding could also be added to the preferred form of arms—those made from Breathoprene™ or similar.

Interface Core Section—General

The interface core section 11 of the preferred forms is formed so as to act as a manifold in use, receiving gases from the supply conduit 19. The connection between the interface core section 11 and the patient or user end of the supply conduit 19 can be made by way of a push-fit connection or similar. In one preferred form (not specifically shown), the interface core section 11 is formed as a one-piece item, and an aperture or connector portion which is adapted to receive the patient end of the supply conduit 19 is formed directly in this one-piece item. In this form, the end of the supply conduit 19 is connected directly to the one-piece interface core section 11—e.g. by pushing it into the aperture located on the interface core section 11, or by connecting it to the connector portion. However, in other preferred forms, this aperture is located on a separate sub-item or sub-assembly that is included as part of the interface core portion 11 when the interface core section 11 is assembled, but is initially formed as a separate item.

Interface Core Section—First Preferred Form

An example of an interface core section 211 that has a manifold section and a connector that is initially formed as a separate item is shown in FIG. 2. The interface core section 211 includes a manifold section 211-1 and an elbow connector 211-2. One end of the elbow connector 211-2 is formed as a ball joint 290, and this locates into a socket 291 on the front of the manifold section 211-1 in use, the socket 291 adapted to act as a gases supply aperture. This allows a degree of three-dimensional relative movement, or movement in more than one plane, between the manifold section 211-1 and the elbow connector 211-2. That is, as well as being able to rotate through 360 degrees in a plane running across the front of a user's face, the elbow connector 211-2 also has a limited degree of up/down rotation and side/side rotation relative to the manifold section 211-1.

Interface Core Section—Second Preferred Form

An example of a second preferred form of interface core section 311 that includes an elbow connector is shown in FIG. 3a. A manifold portion or manifold section 311-1 is shown, the manifold section 311-1 including an aperture located at the front of the manifold section 311-1. An elbow connector 311-2 is connected to the manifold section 311-1 via the aperture, with one end of the elbow connector 311-2 locating into or connected to the aperture, and the other connected to the supply conduit 190. The manifold section 311-1 and the elbow connector 311-2 are mutually adapted to provide a 360 degree swivel—the elbow connector 311-2 and the manifold section 311-1 can swivel or rotate through 360 degrees relative to one another in use, in a plane across the front of a user's face, as shown in FIG. 3b. The manifold section 311-1 and the elbow connector 311-2 are assembled together to form part of the interface core section portion 311 of the embodiment of FIG. 3.

Interface Core Section—Third Preferred Form

Yet another example of an interface core section that includes an elbow connector is shown in FIG. 4. The manifold section 411-1 includes an aperture at one side of the manifold section 411-1. This aperture receives one end of an elbow connector 411-2 in use, the elbow connector 411-2 adapted to rotate freely relative to the manifold section 411-1, the plane of rotation of the elbow connector aligned back-front of a user 2 in use, rather than side-side as in the embodiment of FIG. 3b.

Interface Core Section—Pillow Section

The interface core section 11 also includes a pillow section 50, the pillow section including pillows 50-1 which are adapted to substantially seal against the nares of a user in use. The pillow section 50 is fluidically connected to the manifold section 11-1 so that in use the heated, humidified gases stream enters the pillow section 50 from the manifold section 11 and passes through the pillows 50-1 into the nasal cavity of a user. 'Substantially seals' as it is used in this specification should be taken to mean that perfectly sealing against the nares with no leaks is the most desirable outcome. However, a small degree of leakage in use is almost certainly inevitable, and a person skilled in the art will understand that the phrase 'substantially sealing' is intended to indicate that a very small amount of leakage may sometimes, but not always, occur. As the pillows 50-1 are substantially sealed against the nares of a user, all or substantially all of the stream of gases which passes through the manifold section 11 and the nasal pillow section 50 will be delivered to a user.

As shown in the preferred embodiments of FIGS. 2, 3 and 4, the pillow section 50 is composed of two main sub-parts that form a continuous or integrated whole in use: pillows 50-1, which locate into the nares of the user or patient 2 in use, and a pillow manifold section or pillow gasket 50-2, which is connected to the interface core section 11 in use, so that gases passing through the core section 11 in use will then pass into the pillow gasket 50-2 and from there into the pillows 50-1.

In order to aid in sealing the nasal pillows 50-1 against the nares of a wide variety of users, each of whom will have differently shaped and sized nostrils, the pillows 50-1 are in the preferred form formed from a soft and supple material with a high degree of flexibility, such as silicone rubber or similar. Preferred forms of the nasal pillows 50 are described in detail below.

The nasal pillow section 50 can either be formed separately from the rest of the core portion 11, or integrally formed with the core portion 11. In the preferred embodiments as shown in FIGS. 2, 3 and 4, the nasal pillow section 50 is a separate item to the core portion 11.

The nasal pillow section 50 is formed from two main parts in the three preferred fowls described herein: a base portion or nasal pillow gasket portion 50-2, and nasal pillows 50-1. The attachment or connection of the nasal pillow section 50 to the remainder of the core portion 11 is achieved by attaching the gasket portion 50-2 to the manifold portion 11-1, with the pillows 50-1 preferably (although not always) integrally formed with the gasket portion 50-2. The embodiments of FIGS. 2, 3 and 4 show this form of connection.

In the preferred embodiments, at least the pillows 50-1 are formed from a supple and flexible material, such as silicone rubber.

Pillow Gasket—First Preferred Form

The first preferred form of pillow gasket portion 250-2 shown in FIG. 2 shall now be described with particular reference to FIG. 2c and FIGS. 5, 6 and 7.

The preferred form of pillow gasket portion 250-2 includes an open lower face or open lower front portion 237 which corresponds in use to the open rear face (not shown) of the manifold section 211-1, so that in use it acts as a gases aperture. It should be noted that the open rear face and the open lower portion 237 could be apertures—these do not have to cover the entire 'face'. In use, the perimeter of the open lower portion 237 of the pillow gasket portion 250-2 is connected to the open rear face of the manifold section 211-1. The wall 237a which surrounds the open lower portion 237 slots or locates into the open rear face of the manifold section 211-1, and substantially seals against it. It can be seen that all of the gases passing through the manifold section 211-1 will pass into the pillow gasket portion 250-2 and from there into the nasal pillows 250-1. It should be noted that the pillow gasket portion 250-2 can be attached and removed repeatedly from the manifold portion 211-1 as required by a user. Optionally, if required, a key 238 can be formed into the wall section 237, the key 238 slotting into a corresponding slot in the manifold section 211-1 to ensure the pillows are correctly oriented in use.

In the first preferred form of pillow gasket portion 250-2, the pillow gasket 250-2 is shaped so that the two side portions are slightly angled towards one another. That is, the top surface which covers the open rear face of the manifold 8 appears to have a V-shape when viewed from the front, with the pillows 250-1 one on each of the two sub-surfaces or inner faces of the 'V'. The angle of the 'V' is not acute—each edge or plane of the 'V' of the pillow gasket portion 250-2 is raised by a few degrees only (e.g. 5-10 degrees). The pillows 250-1 are mounted one on each of the two planes, and are in this manner angled inwards towards one another slightly in the most preferred form (although there are of course many other ways in which this could be achieved without creating a 'V'-shape).

In the preferred form, as described above, the nasal pillows 250-1 and the gasket portion 250-2 are formed as a one-piece item. However, the pillows 250-1 could be removably connected to the gasket portion 250-2, either individually or as a pair. For example, the gasket portion 250-2 could include a pair of stub bases to which the pillows are press-fitted in use, the stub base and the base of the stem 250-3 being mutually adapted to connect together by way of a press-fit, a keyed connection, or similar. This would potentially allow pillows which are of different shapes or sizes to be fitted to the pillow gasket portion 250-2. This would be advantageous if a user required pillows moulded specifically to the shape of their nares, or pillows of different sizes. This would also allow a range of standard pillows to be manufactured, the range having different sizes or different shapes, or both. This would provide a range of off-the-shelf adjustment.

In the very most preferred forms, the pillow gasket portion 250-2 is formed so that in normal use, the pillow gasket portion 250-2 is held off or apart from the upper lip of a user 2, the intention being that there is no contact or minimal contact between the gasket portion and the lip of a user in use. When the phrase 'no contact' is used in this specification, it should be taken to mean that there is no intentional contact, and any contact that does occur is outside the intended normal operating condition of the interface. Surprisingly, and in contrast with what has previously been known in this area of the art, it has been found that minimising contact with the upper lip of a user is in certain circumstances beneficial. Some prior art devices have actively used the upper lip as a support for the pillow gasket portion, even in some cases going as far as to have a lower rear portion of the gasket which can be at least semi-inflated by the gases passing through the pillow gasket. It is intended in these designs that the inflated/inflatable lower rear portion acts as a lip cushion and aids in providing support.

Surprisingly however, it has been found that having a pillow gasket which minimises contact with the upper lip of a patient can also be beneficial for some users, and can act to increase the user's comfort levels and compliance with their therapy regime. Surprisingly, it has also been found that movement of a user's upper lip can in some cases have more of detrimental effect on the sealing of pillows against the nares of a user 2 than is known in the art at the present time, or was anticipated. Because this detrimental effect was not anticipated, it was not compensated for when designing the interfaces which are currently known in the art. It has been found that in some cases when using the prior art interfaces that movement of the user's lip causes an excessive amount of movement of the interface core portion and pillows—more than was originally anticipated for interface designs which include lip cushions. Therefore, when using the prior art designs, there is an increased likelihood that the seal between the nares of a user 2 and one or both of the pillows 50 will fail, at least momentarily. The pillows of the present invention offer a useful, new, and surprising alternative to the prior art, with contact between the pillows and the lip minimised as far as possible.

There are several different ways this minimised or no contact can be achieved. The preferred forms will now be described with particular reference to FIGS. 5, 6 and 7.

In the first most preferred form as shown in FIG. 5, the lower inner surface 500 of the pillow gasket portion 250-2 appears inwardly-sloping or concave when viewed directly from one side—the surface is formed to include a concavity. The concavity in this preferred form runs generally between an area at or close to the lower end or base of the stem 253 of the pillows 250-1, and the rear of the wall 237a (however, it should be noted that the concavity could run between any convenient points—it does not have to be restricted to these points). This concavity ensures that contact between the users face and the pillow section 250 occurs only at the nasal pillows 250-1 during the majority of usage, and there is no contact in use with the upper lip of a user 2, or that what contact does occur is minimised.

Figure 5D:
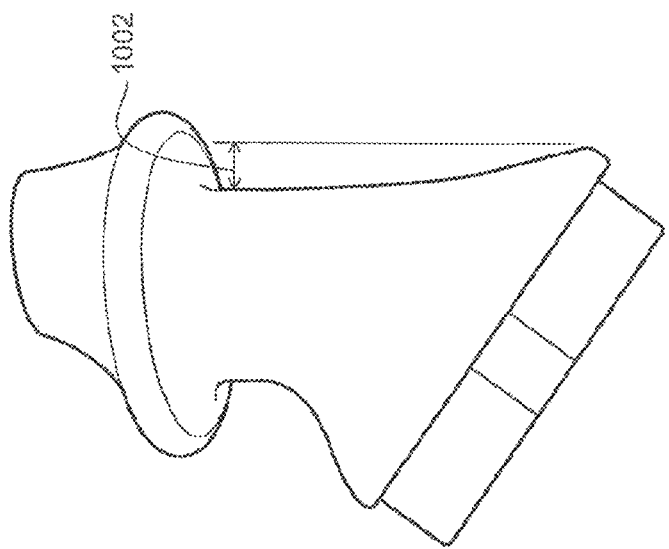
FIGS. 5c and 5d show the nasal pillow section of FIGS. 5a and 5b, with dimension lines added to show the critical dimensions.
Figure 5C:
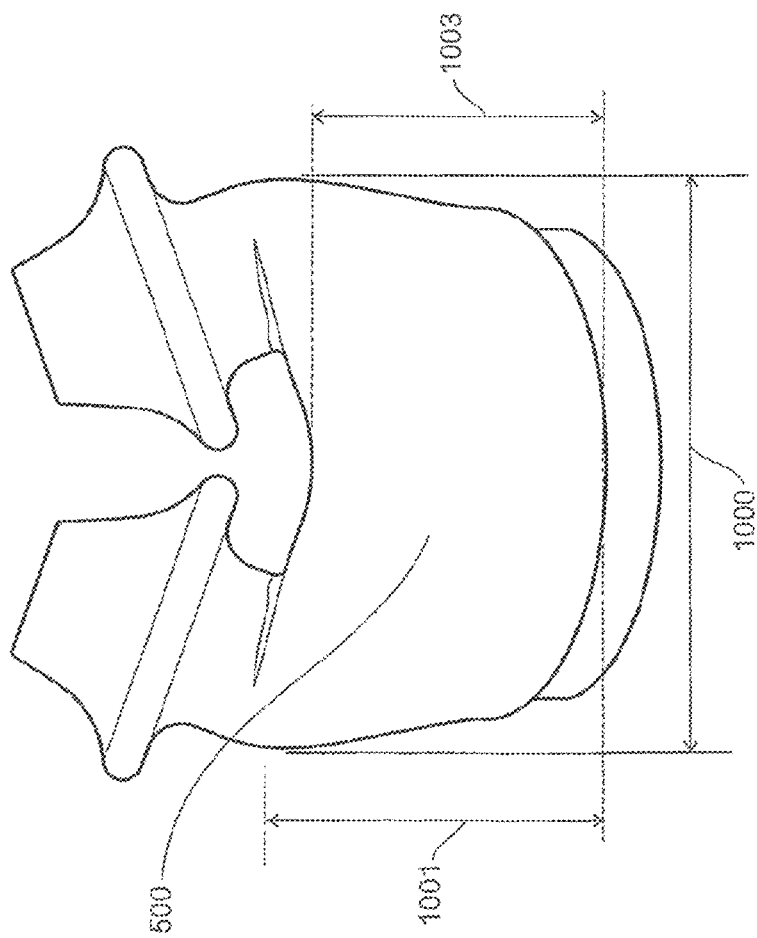

The critical dimensions of the very most preferred form are shown in FIGS. 5c and 5d. Dimension line 1000 on FIG. 5c shows the width dimension across the lower inner face 500 of the pillow section 250 for the very most preferred form, this being 40 min. Dimension line 1001 on FIG. 5c shows the preferred height of the face 500 between the base of the pillows 250 on the outer side, and the wall 237 for the very most preferred form, this being 26.5 mm. Dimension line 1003 on FIG. 5c shows the preferred height of the face 500 between the base of the pillows 250 on the inner side, and the wall 237 for the very most preferred form, this being 24.5 mm. Dimension line 1002 on FIG. 5d shows the inner curve of the concavity for the face, showing that the upper edge of the face 500 is 3 mm further forward than the lower edge of the face 500 in the most preferred form. It should of course be noted that these dimensions are the dimensions of the most preferred form, and a range of e.g. 5 mm and possibly up to 10 mm or more either side of these dimensions is possible.

The lower inner surface 500 could alternatively be a substantially straight planar surface running between the lower end or base of the stein 253 and the rear of the wall 237a. That is, this forward end or edge of the plane in the embodiment of FIG. 2 will be just behind the lowest part of the gases supply aperture 291. However, concave is preferred for this first most preferred form, as this provides the most room for movement of the upper lip of a user 2 without contact occurring.

It can be seen that the planar surface will be at an angle to the vertical—it will be forward-sloping, with the lower edge forward of the rear edge, the angle of slope dictated to a great extent by the locations of the gases supply aperture of the manifold section, and the lower end or base of the stems. It should be noted that the plane does not have to begin and end at these positions, but it is preferred that the edges are substantially at these positions.

As shown in FIG. 5a, the first preferred form of pillows 250 also includes a bridging platform 254 which runs between the stems 253 of the pillows 250-1. The bridging platform 254 helps to localise as much of the movement of the pillows to the region closest to the user's nares. This localisation of the movement assists in helping to avoid any leaks that may develop from the patient moving their lip while wearing the interface. The bridging platform 254 is an area between the pillows that is stiffer than the remaining material around the base of the stems 253, the stems 253 themselves, and the caps 255 of the pillows. In the most preferred form, the bridging platform 254 is created by thickening an area—that is, using a thicker material in that area or section to increase the stiffness in that area. Surprisingly, it has been found that making the lower rear surface 500 concave as described above and also combining this with the bridging platform such as platform 254 provides unexpected benefits. The concave surface can be shaped in such a manner as to minimise contact between the user's lip and the surface 500, and also so that the platform 254 is supported and movement of the pillows 250-1 is localised.

In the embodiment shown in FIG. 5, the stems 253 are flared towards their top end, where the stems 253 meet and merge with the bottom of the caps 255. It should be noted that if required, the stems 253 could alternatively be straight-sided, or at least not flared towards the top end.

Figure 6A:
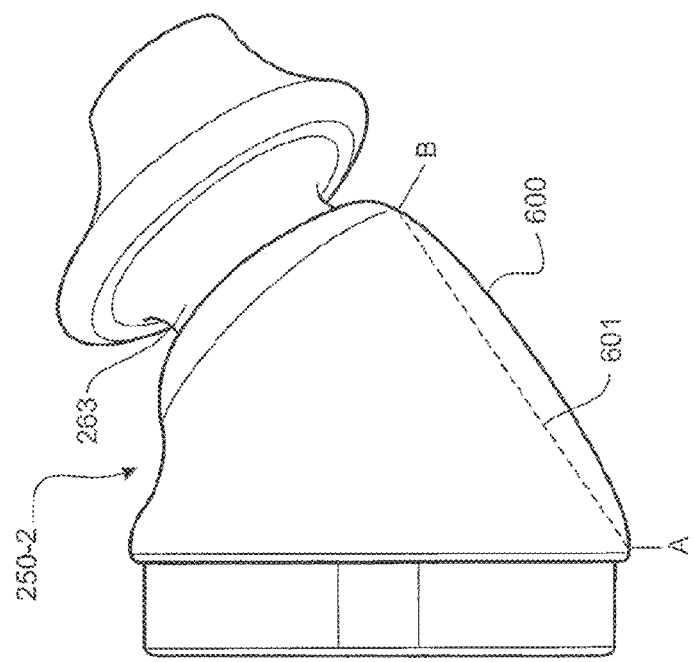
FIG. 6a shows a second preferred form of nasal pillow section for use as part of either of the first or second preferred embodiments of interface assembly as shown in FIG. 2 or 3, the nasal pillow section having a nasal pillow gasket section and nasal pillows connected to the nasal pillow gasket section, the nasal pillow section shown being viewed from the rear looking forwards.
Figure 6B:
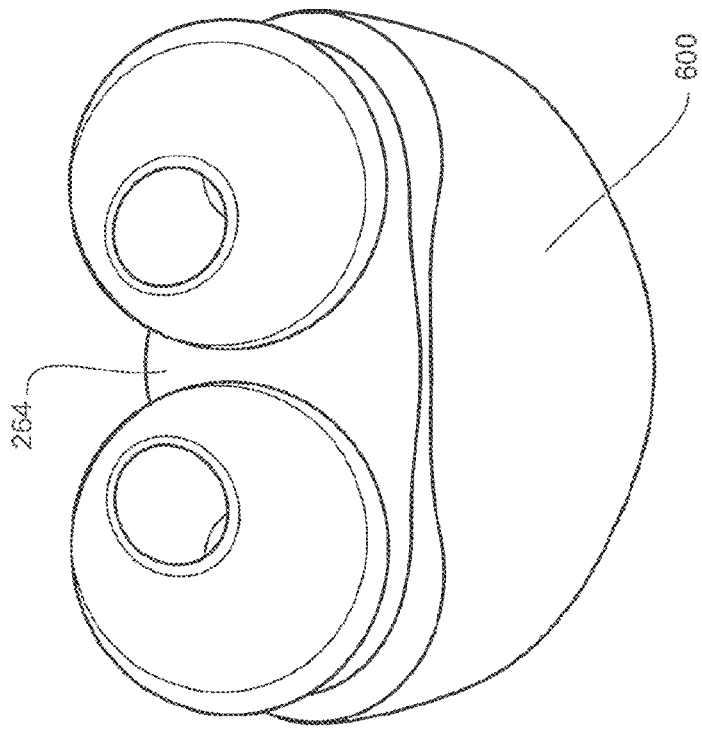
FIG. 6b shows the nasal pillow section of FIG. 6a, viewed from a user's right hand side if the nasal pillow section were in use.

The second most preferred form will now be described with reference to FIG. 6. The second most preferred form is very similar to the first most preferred form described above with reference to FIG. 5. However, as can be seen from FIG. 6b, the lower rear surface 600 or support structure 600 is very slightly outwardly sloped or slightly convex. In this context, slightly outwardly sloped or slightly outwardly bowed is defined as follows: the surface 600 never deviates more than 3 mm outwards from a straight line drawn between the two ends (i.e. if a straight line 601 were drawn between point A and point B on FIG. 6b, this line can be thought of as defining a plane passing across the rear of the actual pillow gasket portion 250-2. For the actual pillow gasket portion 250-2, stating that the surface 600 is slightly outwardly sloped means that there is never a deviation of more than 3 mm from the plane defined by line 601 for the actual pillow gasket portion 250-2 when it is manufactured.

In a similar fashion as for the first most preferred form described above with reference to FIG. 5, the second preferred form also includes a bridging platform—bridging platform 264—which runs between the stems 263 of the pillows 250-1. The combination of the bridging platform 264 and surface 600 is similar to that described above: in combination these elements can be formed so that not only is contact between the lip of a user 2 and the interface minimised, but also the platform 264 is supported and movement of the pillows 250-1 is localised.

Figure 7B:
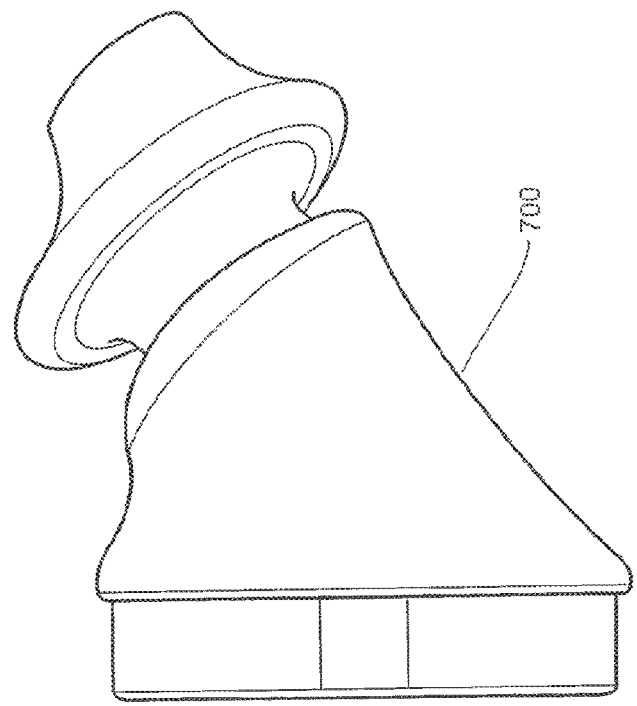
FIG. 7b shows the nasal pillow section of FIG. 7a, viewed from a user's right hand side if the nasal pillow section were in use on the face of the user.
Figure 7A:
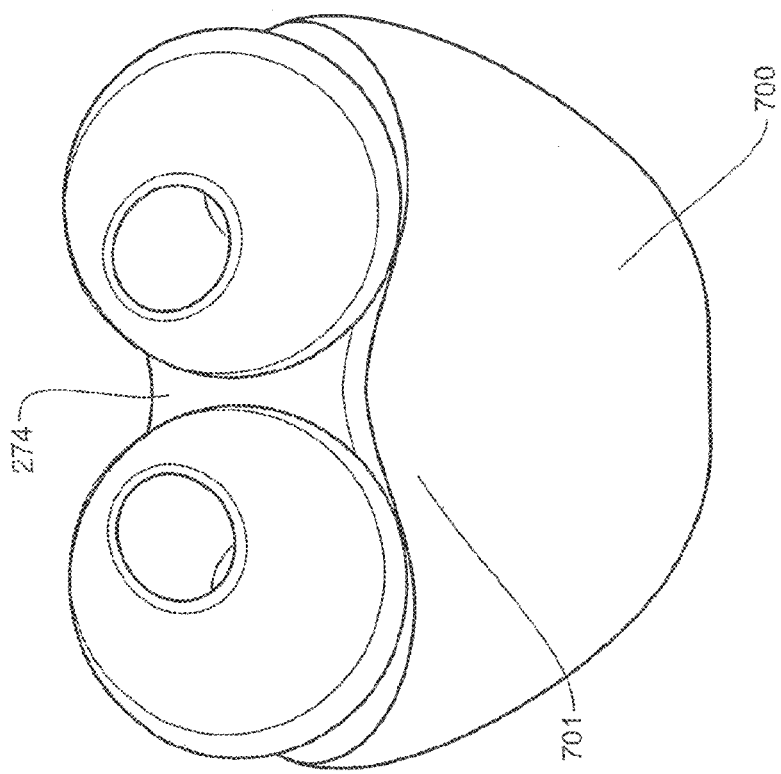
FIG. 7a shows a third preferred form of nasal pillow section for use as part of either of the first or second preferred embodiments of interface assembly as shown in FIG. 2 or 3, the nasal pillow section having a nasal pillow gasket section and nasal pillows connected to the nasal pillow gasket section, the nasal pillow section shown being viewed from the rear looking forwards.

The third preferred form of pillow gasket will now be described with reference to FIG. 7. FIGS. 7a and 7b show a design that is very similar to that of FIG. 5. This form or embodiment is slightly different to that shown in FIGS. 5a and 5b as it has a bridging platform 274 that sits as far away from the lip as possible without compromising the localised movement of the pillows provided by the bridged platform design. This is achieved by including an indented profile 701 as part of the design. This has the surprising advantage that the inwardly sloping support face or concave face 700 in combination with the indented profile 701 of the bridging platform 274 will minimise contact between the elements of the interface and the face of a user, and still provide sufficient support.

It should be understood that there are several other design requirements for a patient interface, and in particular the interface core section and pillows, aside from increasing user comfort and compliance by minimising contact with the users upper lip (where this minimised contact is considered to be appropriate or beneficial). For example, as well as user comfort, there is the requirement that a good seal is formed between the pillows and the nares, that the pillows and gasket form an internal gases passageway that is of a size and shape to allow the passage of heated humidified gases without overly impeding the gases flow and without causing gases flow or pressure to be outside a desirable range, etc. A person skilled in the art, having access to the description relating to the preferred embodiments as outlined above and below, would be able to ascertain e.g. the exact dimension or shape which they require from within a suitable range, which would have the desired overall effect.

Pillow Gasket—Second Preferred Form

Figure 3C:
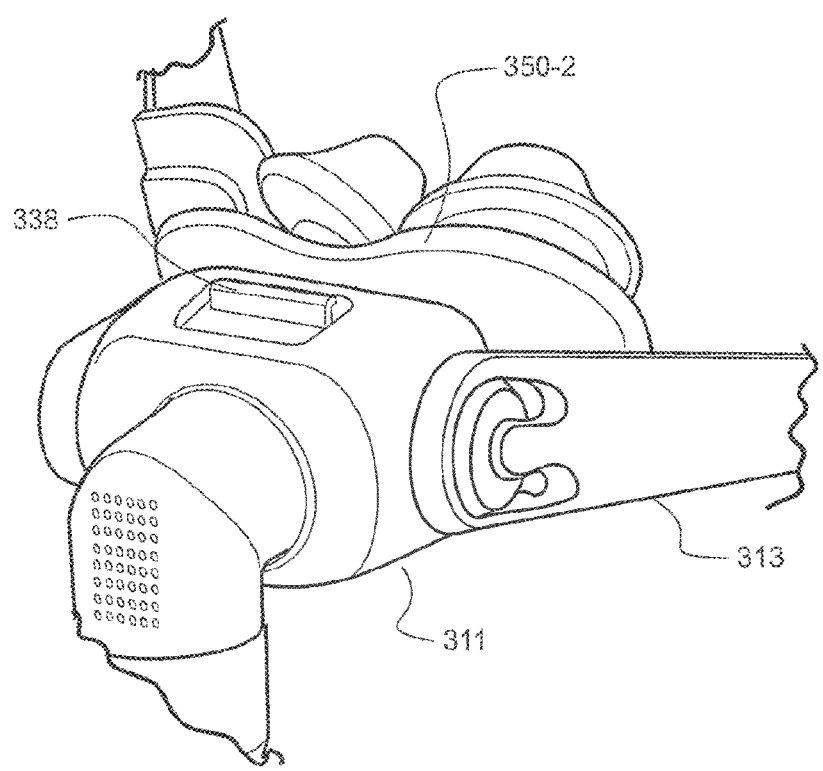
Figure 4A:
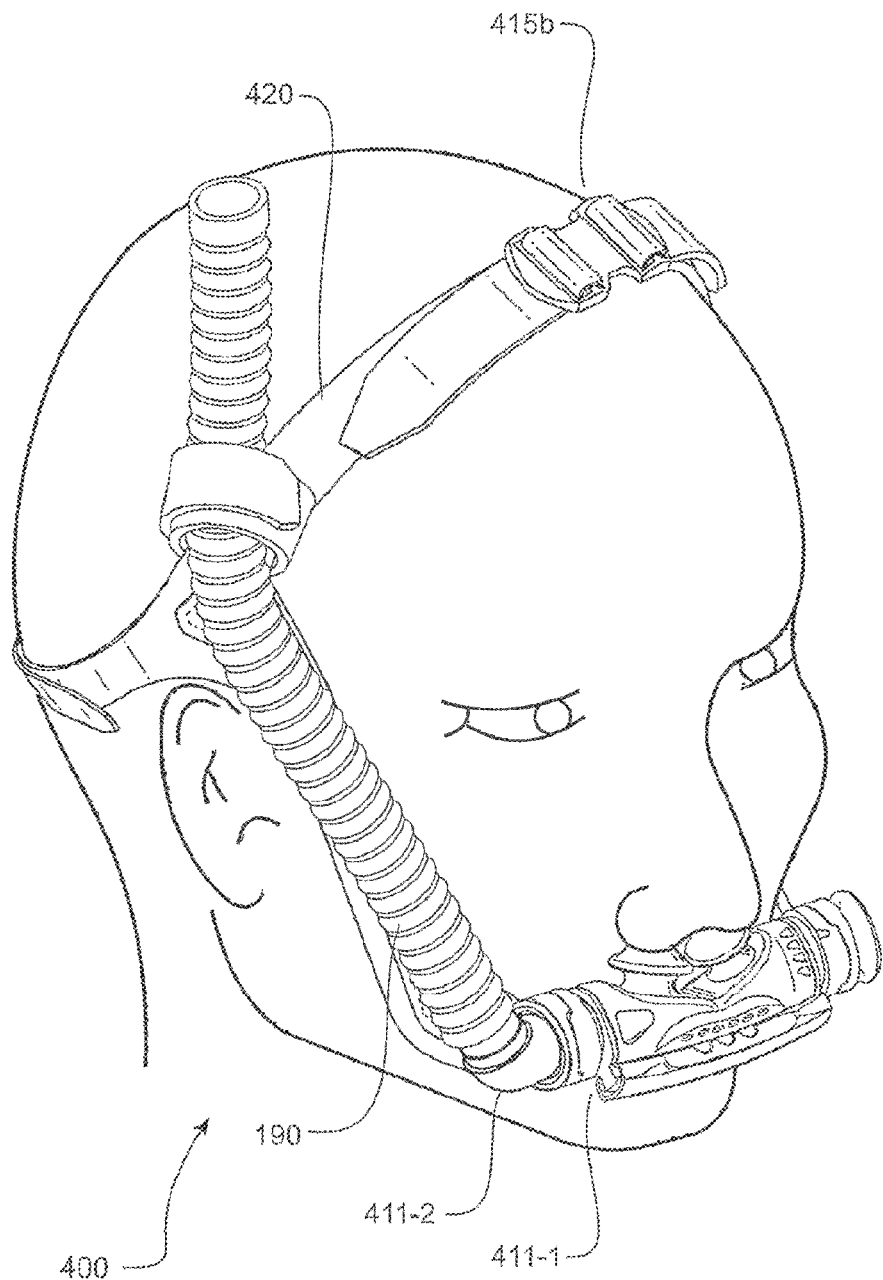
FIG. 4a shows a third preferred embodiment of the interface assembly of the present invention in use being worn by a user, the interface assembly of this third preferred form having similar elements to those of the preferred embodiments of FIGS. 2 and 3, but configured slightly differently.

The second preferred form of pillow gasket is shown in FIG. 3, and is described below with particular reference to FIG. 3c. This second preferred form shares many of the features of the first preferred form, including the three preferred forms of pillow gasket portion described above. That is, the pillow gasket portion 350-2 of this second preferred form can include features such as for example the surfaces 500, 600 and 700 and the indented profile 701 as described above, and these are dimensioned in a similar fashion to the preferred foiin 250 described above. As described above, the manifold section 311-1 includes an aperture located at the front of the manifold section 311-1, where an elbow connector 311-2 is connected to the manifold section 311-1. The forward end or edge of the forward-sloping plane in the embodiment of FIG. 3 will be just behind the lowest part of this gases supply aperture.

The main difference between the pillow gasket portion 250-1 and the pillow gasket portion 350-2 is that the second preferred form of pillow gasket 350-1 is held in position on the manifold section 311-1 by a pair of protrusions 338 on the gasket portion 350-2 which slot into corresponding apertures on the manifold section 311-1. In the form shown in FIG. 3c, the protrusions 338 and the apertures are aligned centrally on the manifold section 311-1 and the gasket portion 350-2. However, this potentially allows the gasket portion 350-2 to be fitted upside-down on the manifold section 311-1, so if required these can be offset to the sides, so that the gasket portion 350-2 can only be connected in one (correct) orientation.

Pillow Gasket—Third Preferred Form

Figure 4B:
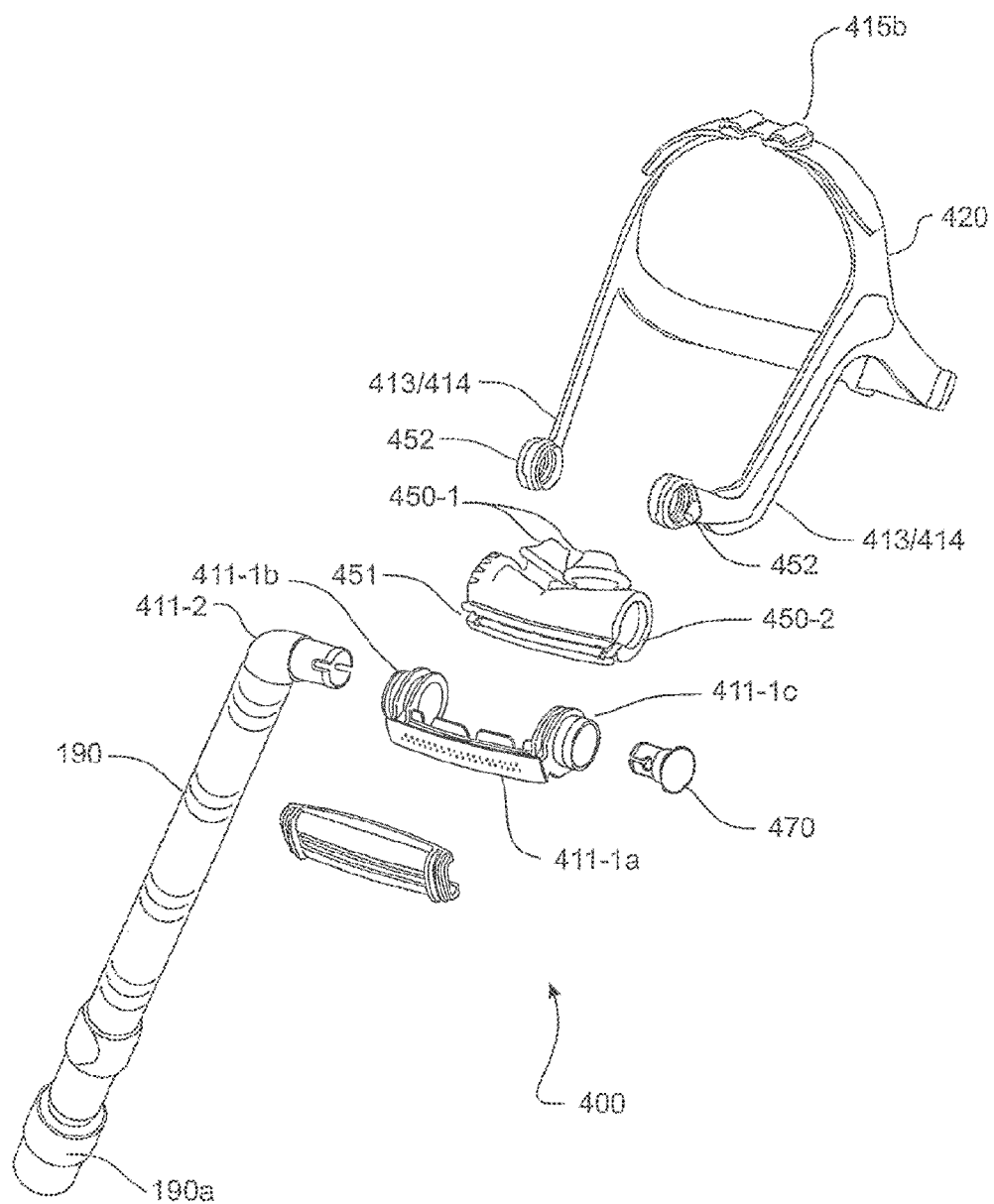
Figure 8A:
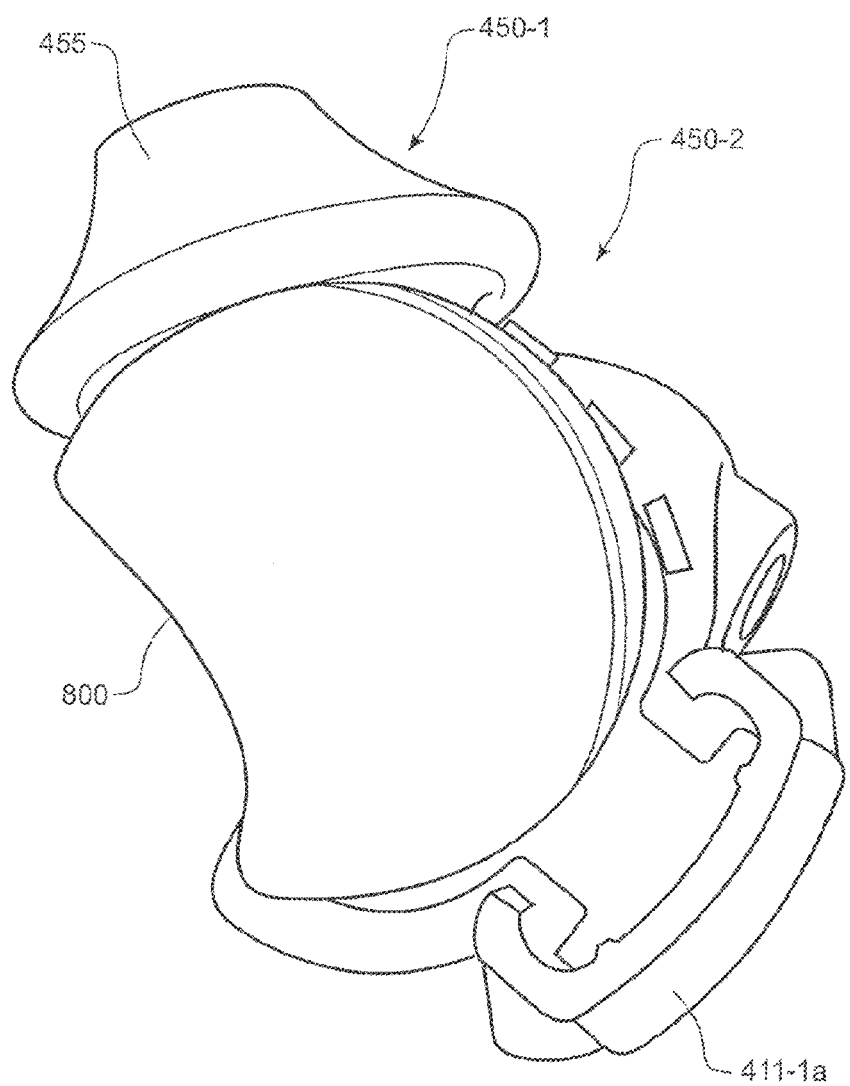
FIG. 8a shows a side view of a fourth preferred form of nasal pillow section for use as part of the third preferred embodiment of interface assembly as shown in FIG. 4.

A third preferred form of pillow gasket is shown in FIG. 4, and is described below with particular reference to FIG. 4b and FIGS. 8a and 8b.

The manifold section 411-1 and the main body of the gasket section 450-2 of the pillow section 450 of this third preferred form when assembled for use have the overall general form of a cylinder, which in use is aligned across the top lip of a user. The manifold section 411-1 includes an aperture at one side of the manifold section 411-1, formed in the end section 411-1b, the aperture adapted to receive one end of the elbow connector 411-2 in use. The elbow connector 411-2 and the manifold section 411-1 are adapted to rotate freely relative to each other in use, the plane of rotation of the elbow connector aligned back-front of a user 2 in use, rather than side-side as in the embodiment of FIG. 3.

In this third preferred form, the pillow section 450 is removably attached to manifold section 411-1. When the pillow section 450 and the manifold section 411-1 are connected, the two nasal pillows 450-1 extend outwards and upwards from the cylindrical main portion, towards the nares of a user 2 in use.

The manifold section 411-1 is formed from a semi-rigid plastic, with a central cross-brace body section 411-1a, and two end sections 411-1b and 411-1c. A cap 470 closes off one end—end 411-1c—in use (the opposite end from the elbow connector 411-2).

The gasket section 450-2 of the pillow section 450 has the general overall form of a cylinder, the gasket section 450-2 and the manifold section 411-1 mutually sized so that the gasket section 450-2 slots between the end sections 411-1b and 411-1c. The gasket section 450-2 includes a slit 451 which runs along the length of the cylindrical body, at the bottom front of the cylindrical body, opposite the pillows 450-1. In use, the slit 451 in the gasket section 450-2 is held closed by engagement of the edges of the slit with the cross-brace body section 411-1a.

The ends of the headgear straps 413/414 in this third preferred form include connectors 452 which engage with the ends of the manifold section 411-1 to hold the manifold section and pillow section 450 in place on the face of a user in use.

Figure 8C:
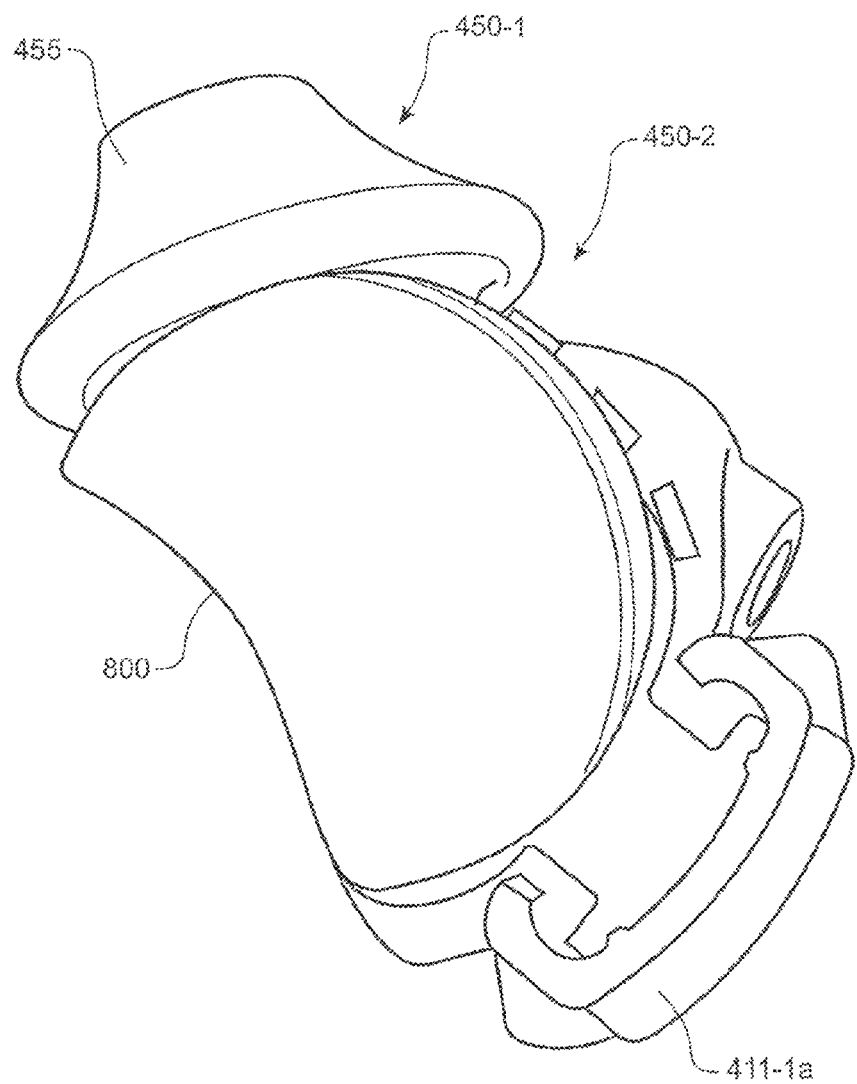

In a similar manner to that described above for the first and second preferred forms or preferred embodiments, the lower rear part of the gasket section 450-2 can if required) be rounded inwards in a concave fashion, so that there is no contact between the upper lip of a user 2 and the rear of the gasket portion 450-2 of the pillow section 450 of the third preferred form. One way in which this concavity can be achieved is shown in FIG. 8, with the lower inner surface 800 concave or curved inwards. FIG. 8a shows one style of concavity, the surface 800 re-curving outwards at the lower part of the concavity, towards the bottom or lower portion of the gasket portion 450-2. FIG. 8c shows a second style of concavity, with the lower part or portion of the surface 800 ending closer to the lower inner edge or side of the slit 451 than the first style shown in FIG. 8a.

Figure 8D:
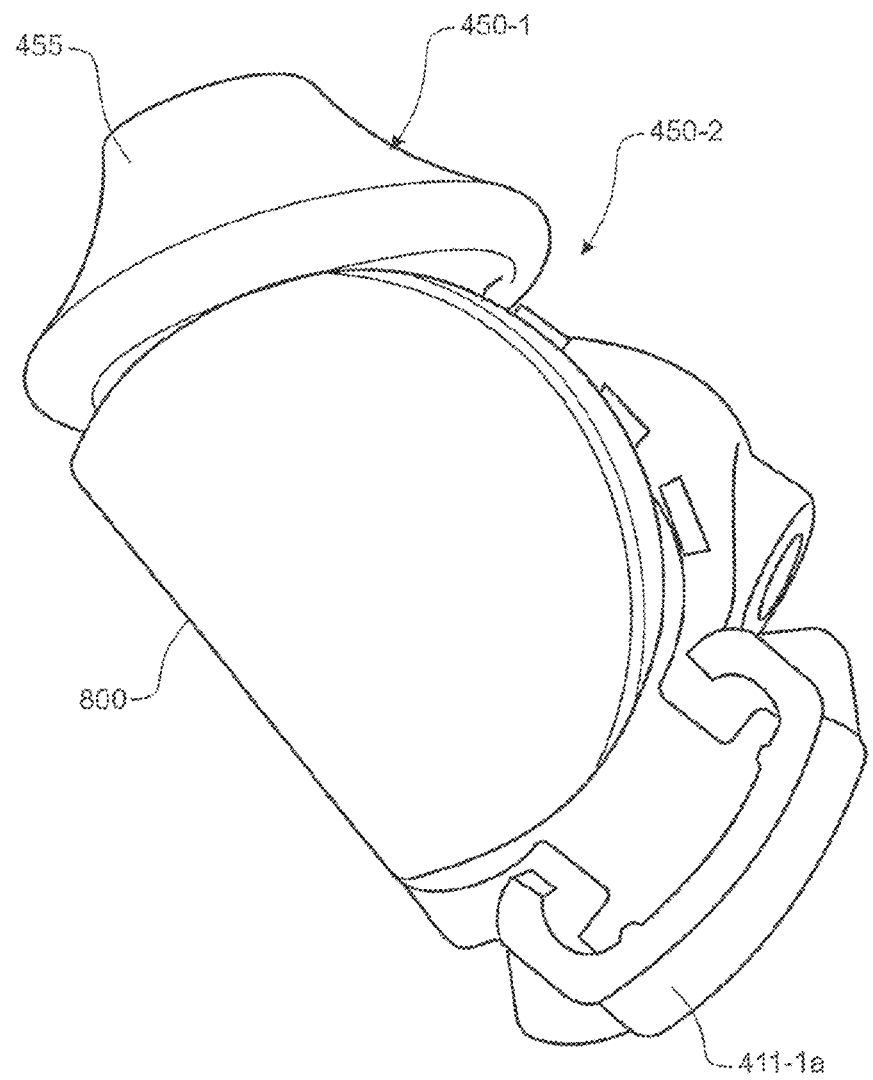

In a similar manner to the first and second preferred forms, the concavity is intended to minimise contact in use with the upper lip of a user 2. The lower inner surface 800 could alternatively be a straight planar surface running between the lower end or base of the stems 453 and the lower inner edge or side of the slit 451, or another appropriate point or plane running across the rear of the gasket portion 450-2—for example, the outer, lower edge of the planar surface could be substantially close to the lowermost point of the gases supply aperture formed in the end section 411-1b (which is also substantially close to where the lower inner edge or side of the slit 451 is located). One 'straight surface' example is shown in FIG. 8d. However, concave is preferred (as in FIGS. 8a and 8c), as this provides the most room for movement of the upper lip of a user 2 without contact occurring.

A bridging platform (not shown) can also be used in a similar fashion to the bridging platforms 254, 264, 274 as described above in relation to the first and second gaskets. The bridging platform can include an indented profile if required, similar to that already described.

The stems 453 for this form are shown as flared towards their top end, where the stems 453 meet and merge with the bottom of the caps 455. It should be noted that if required, the stems 253 could alternatively be straight-sided, or at least not flared towards the top end.

Pillows

As described above, there are three particularly preferred forms of interface assembly, which have several common elements and several elements which are unique to that particular preferred form. Many different forms of pillow design can be used with the preferred embodiments described above. For example, the pillows shown in the preferred embodiments of FIGS. 1 to 8 all have a single-walled cap 55 and a smooth-walled stem 53, the stem flaring at the upper end, towards the cap 55.

It should be noted that different designs of pillow can be used with the preferred forms of interface assembly as described above. For example, the stems or stalks 53 could be ribbed, as described in co-pending U.S. application 61/060,855, the contents of which are incorporated by reference.

Also, if required, pillows having a double-cap structure (an inner cap and an outer cap) could be used.

It should also be noted that a 'single pillow' structure could be used, with one pillow or item delivering gas to the nostrils of a user—for example, a pillow structure with a single stem that bifurcates into two caps just below the nostrils, or a single cap shaped to deliver gas to both nostrils simultaneously, the single cap being fed a gases stream through either a single or a double stem. 'Nasal pillows' in this specification should be read as covering at least these different possible designs, and not just the paired stalk and cap arrangement described above. 'Nasal pillows' in this specification should also, if appropriate, be taken to mean a nasal mask—for example, a silicone nasal mask fluidically connected to the gasket, the gasket in use being located underneath the nostrils of a user and in front of the upper lip of a user. The nasal mask ('nasal pillows') would extend from the gasket, covering around at least part of the outside surface of the nose of a user and substantially sealing against the skin of a user so that the stream of heated humidified gases is delivered to the nare of the user.

The features described above can be used individually or in any combination in the pillows and interface of the present invention.

Lexicon

'Supple' or 'flexible' as these words are used in this specification with reference to e.g. the nasal pillows should be taken to mean that the item can be substantially and repeatedly deformed—e.g. by a user pinching, squashing or crushing it in their hand, with the item returning to its original shape with little to no plastic deformation occurring. An item having a rectangular or square cross-section, with a thickness of 1-2 mm, a width of e.g. 1 cm, and a length of 5 cm or more, formed from a 'supple' or 'flexible' material as it should be understood in this specification, will, if held at one end, bend to an extent easily appreciable to the naked eye—i.e. it will bend at least 2-3 mm. The most preferred materials having 'supple' or 'flexible' properties as they should be understood within the context of this specification will, if formed in the manner referred to above, bend completely—that is, bending enough so that the unsupported end points substantially directly downwards. If the material does not bend to an appreciable extent, then it is a rigid or semi-rigid material for the purposes of this specification—see below. It should also be understood that 'flexible' is intended to mean a material that is soft, supple and flexible enough that an item formed with the dimensions outlined above (1-2 mm.times.10 mm.times.50 min) could be rolled into a solid tube (i.e. with no central 'hollow' portion), and when the tube is unrolled there would be little to no plastic deformation of the material.

'Rigid' or 'semi-rigid' as it is used in this specification should be understood to mean that an item described in this manner can be elastically deformed, but that it would require application of an external force apart from gravity (i.e. more than its own weight) to do so—a 'rigid' or 'semi-rigid' item will not collapse or bend under its own weight, in any orientation. It is noted that all items usually described as rigid do have a certain degree of elasticity, but the elastic limit will normally be reached before the elastic deformation of the rigid material is appreciable to the naked eye. Glass, for example, will shatter before the average person is able to appreciate that it has elastically deformed at all. An item having rectangular or square cross-section, with a thickness of 1-2 mm and a length of up to 10 cm, formed from a 'rigid' or 'semi-rigid' material as it should be understood in this specification, will not bend to an extent easily appreciable to the naked eye. As an example, the arms of the Fisher & Paykel Opus™ interface or the ResMed Mirage Swift™ II interface are around 10-11 cm long and have a thickness of less than 1 mm. The arms of these devices are formed from a plastic having a rigidity so that they will not bend under their own weight if held at one end, and for the purposes of this specification can be considered to be 'rigid' or semi-rigid'.

'Substantially vertically downwards' as it is written in this specification should be interpreted as not necessarily meaning absolutely vertical—an angle of 10-20 degrees or more off-vertical lies within the meaning of 'substantially vertical' as it is used in this specification.

It should also be noted that 'downwards', 'outwards', 'inner', 'outer', 'rear', 'front', and similar terms as they are used in this specification refer to the mask being worn by a user who is standing up. For example, 'inner' and 'rear' refer to that side of the interface nearest a users face in use. However, in use the interface is intended to be used by a user who is asleep and will be lying on a bed, either on their back, front or side. The convention referred to above (a user standing) has been adopted for ease of reference.

It should also be noted that the term 'interface' or 'interface assembly' as it is used in this specification refers to any combination of the interface core section 11 (or 211, 311 or 411), the interface conduit 19 or supply conduit 190 (or both), and the headgear assembly 12—that is, for the preferred embodiment, the term 'interface' could refer to the interface core section 11 with or without the headgear assembly 12, and with or without the supply conduit 19.

The terms 'swivel' and 'rotate' have their normal dictionary definitions. However, it should specifically be noted that as used in this specification, 'rotate' means that the item turns around an axis or centre point and movement is in a single plane. In contrast, 'swivel' as used in this specification should be taken to mean that the item is capable of movement in more than one plane.

What is claimed is:

1. A nasal pillow member for use with an apparatus for providing a stream of gases to a user, the nasal pillow member located in front of an upper lip and sealed to nares of a user in use, the nasal pillow member comprising:
   first and second nasal pillows each comprising a distal end, a proximal end, and a stem portion extending from the distal end to the proximal end, the proximal end having an outlet aperture and a flared portion surrounding the outlet aperture, the flared portions being configured to substantially seal against nares of a user in use, the stem portion begin narrower than the flared portion; and
   a pillow gasket portion formed with the first and second nasal pillows as a single piece of supple material, the pillow gasket portion comprising a manifold having a distal end with a gases aperture and a proximal end, the gases aperture receiving a stream of gases in use, the gases aperture comprising a wall which surrounds an open lower front portion of the gases aperture, the proximal end of the manifold comprising a bridging portion defining first and second planar side areas, the first and second planar side areas oriented at an angle relative to each other, forming a v-angle when viewed from a front side of the pillow gasket portion, the distal ends of the first and second nasal pillows being connected to the first and second planar side areas such that the stem portions of the first and second nasal pillows extend from the first and second planar side areas in directions angled toward each other;
   the manifold comprising a lower inner surface oriented to face towards an upper lip of a user in use, the lower inner surface comprising a lower distal end portion disposed at the distal end of the manifold, a lower proximal end portion disposed at the proximal end of the manifold and a lower middle portion connecting the lower distal end portion and the lower proximal end portion, the lower inner surface having a first length extending from the distal end of the manifold to the proximal end of the manifold;
   the lower inner surface comprising a first rounded convex shoulder at the lower distal end portion and a second rounded convex shoulder at the lower proximal end portion, and wherein the lower middle portion comprises only a single, inwardly curved lower concavity extending from the first rounded convex shoulder to the second rounded convex shoulder, wherein the lower inner surface is at an angle to a vertical, so as to be forward sloping;
   wherein the manifold further comprises an upper surface on a side of the manifold opposite to the lower inner surface and oriented to face away from an upper lip of a user in use, the upper surface comprising an upper distal end portion disposed at the distal end of the manifold, an upper proximal end portion disposed at the proximal end of the manifold and an upper middle portion connecting the upper distal end portion and the upper proximal end portion, the upper surface having a second length extending from the distal end of the manifold to the proximal end of the manifold, wherein the second length is shorter than the first length;
   wherein the upper surface comprises a third rounded convex shoulder at the upper distal end portion and a fourth rounded convex shoulder at the upper proximal end portion, and wherein the upper middle portion comprises only a single, inwardly curved upper concavity extending from the third rounded convex shoulder to the fourth rounded convex shoulder.

2. The nasal pillow member of claim 1, wherein the angle of first and second planar side areas relative to each other is not acute.

3. The nasal pillow member of claim 1, wherein each of the first and second nasal pillows comprises a cap, wherein the first and second nasal pillows are angled rearwards towards one another.

4. The nasal pillow member of claim 3, wherein each cap is a single walled cap.

5. A nasal pillow section for use as part of an apparatus for providing gases to a user, the nasal pillow section being configured to be located in front of an upper lip and below nostrils of a user, in use, the nasal pillow section, when viewed from a front and to one side and being worn by the user who is standing, comprising:
   a pillow gasket comprising:
      an open lower front portion and a lower rear surface, wherein the open lower front portion comprises a gases aperture configured to receive a stream of gases in use, the open lower front portion also comprising a wall surrounding the open lower front portion and oriented to face against an open rear face of a manifold, in use;
      the lower rear surface comprising a forward edge adjacent a lowest part of the gases aperture, the lower rear surface of the pillow gasket being concave such that in use, contact between the upper lip of the user and the pillow gasket is minimized, the lower rear surface having a width extending from a first outer end of the pillow gasket to a second outer end of the pillow gasket,
      wherein the lower rear surface is at an angle to vertical, so as to be forwardly sloping, with a lower edge of the lower rear surface disposed forward from a rear edge of the lower rear surface; and
   nasal pillows fluidically connected to the pillow gasket, adapted to seal against the nostrils of a user in use, and configured to guide gases from the pillow gasket, through the nasal pillows, and to the user, wherein each of the nasal pillows comprise a cap and a stem portion, wherein the nasal pillows are angled rearwardly, towards one another,
   wherein a width extending between from a first outer end of the stem portion of the first nasal pillow to a second outer end of the stem portion of the second nasal pillow is at least as large as the width of the lower inner surface.

6. The nasal pillow section of claim 5, wherein a top surface of the pillow gasket has a V-shape when viewed from the front, with the nasal pillows on each of two sub-surfaces of the V-shape, an angle of the V-shape not being acute.

7. The nasal pillow section of claim 5, wherein the nasal pillows and the pillow gasket are formed as one piece.

8. The nasal pillow section of claim 7, wherein the lower rear surface runs between bases of respective stems of the nasal pillows and a lower rear part of the open lower front portion.

9. The nasal pillow section of claim 8, wherein a height of the lower rear surface between an outer side of the nasal pillows and the lower rear part of the open lower front portion is between 20 mm and 30 mm.

10. The nasal pillow section of claim 9, wherein a height of the lower rear surface between a rear side of the nasal pillows and the lower rear part of the open lower front portion is between 20 mm and 30 mm and less than the height of the lower rear surface between the outer side of the nasal pillows and the lower rear part of the open lower front portion.

11. The nasal pillow section of claim 5, wherein the lower rear surface has a width of between 30 mm and 50 mm.

12. The nasal pillow section of claim 5, wherein each cap is a single walled cap, wherein each of the nasal pillows comprises a smooth-walled stem, the smooth-walled stem flaring at the upper end, towards each cap.

13. A nasal pillow section for use as part of an apparatus for providing gases to a user, the nasal pillow section being configured to be located in front of an upper lip and below nostrils of a user, in use, the nasal pillow section, when viewed from a front and to one side and being worn by the user who is standing, comprising:
   a pillow gasket comprising:
      an open lower front portion and a lower rear surface, wherein the open lower front portion comprises a gases aperture configured to receive a stream of gases in use, the open lower front portion also comprising a wall surrounding the open lower front portion and oriented to face against an open rear face of a manifold, in use;
      the lower rear surface comprising a forward edge adjacent a lowest part of the gases aperture, the lower rear surface of the pillow gasket being concave such that in use, contact between the upper lip of the user and the pillow gasket is minimized,
   wherein the lower rear surface is at an angle to vertical, so as to be forwardly sloping, with a lower edge of the lower rear surface disposed forward from a rear edge of the lower rear surface; and nasal pillows fluidically connected to the pillow gasket, adapted to seal against the nostrils of a user in use, and configured to guide gases from the pillow gasket, through the nasal pillows, and to the user, wherein each of the nasal pillows comprise a cap and the nasal pillows are angled rearwardly, towards one another, wherein the lower rear surface runs between bases of respective stems of the nasal pillows and a lower rear part of the open lower front portion, wherein a rearwards curve of the lower rear surface is 3 mm from a lower edge to an upper edge.

* * * * *